(12) United States Patent
Bottarel et al.

(10) Patent No.: US 10,177,759 B2
(45) Date of Patent: Jan. 8, 2019

(54) SWITCHING CIRCUITRY, RELATED METHOD AND INTEGRATED CIRCUIT

(71) Applicant: STMicroelectronics S.R.L., Agrate Brianza (IT)

(72) Inventors: Valeria Bottarel, Novara (IT); Sandro Rossi, Pavia (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 188 days.

(21) Appl. No.: 15/193,600

(22) Filed: Jun. 27, 2016

(65) Prior Publication Data

US 2017/0310320 A1    Oct. 26, 2017

(30) Foreign Application Priority Data

Apr. 26, 2016  (IT) .................. 102016000042510

(51) Int. Cl.
| | |
|---|---|
| *H03K 17/687* | (2006.01) |
| *A61B 8/00* | (2006.01) |
| *H03K 5/08* | (2006.01) |
| *H03K 17/74* | (2006.01) |

(52) U.S. Cl.
CPC ......... *H03K 17/687* (2013.01); *A61B 8/4494* (2013.01); *H03K 5/08* (2013.01); *H03K 17/6874* (2013.01); *H03K 17/74* (2013.01)

(58) Field of Classification Search
CPC .. H03K 17/687; H03K 17/6874; H03K 17/74; H03K 5/08; A61B 8/4494
USPC ......................................................... 327/108
See application file for complete search history.

(56) References Cited

U.S. PATENT DOCUMENTS

| | | |
|---|---|---|
| 2005/0146371 A1 | 7/2005 | Wodnicki |
| 2006/0034138 A1 | 2/2006 | Bolz et al. |
| 2010/0152587 A1 | 6/2010 | Haider et al. |
| 2014/0145781 A1 | 5/2014 | Taylor et al. |
| 2016/0043720 A1 | 2/2016 | Kubota et al. |

*Primary Examiner* — Ryan Jager
(74) *Attorney, Agent, or Firm* — Seed IP Law Group LLP

(57) ABSTRACT

Switching circuitry includes first and second transistors in series between two terminals and including a common control node with a capacitance between the common control node and an intermediate point. A control circuit includes first and second circuits configured to charge and discharge the capacitance as a function of first and second control signals. The control circuit includes a third circuit having a plurality of diodes and a switch that operates when the voltage at the capacitance is greater than a threshold two diodes in cascade between the intermediate point and the common control node to enable current flow from the intermediate point to the common control node. When the voltage at the capacitance is smaller than the given threshold two diodes are connected in series between the common control node and the intermediate point to enable current flow from the common control node to the intermediate point.

22 Claims, 20 Drawing Sheets

SWITCHING CIRCUITRY, RELATED METHOD AND INTEGRATED CIRCUIT

BACKGROUND

Technical Field

Embodiments of the present disclosure relate to high-voltage switching circuitry, such as integrated high-voltage switching circuitry.

Description of the Related Art

Conventional echography systems comprise one or more ultrasonic transducers, usually an array of ultrasonic transducers, that are used to transmit an ultrasound beam and then receive the reflected beam from a target object.

For example, FIG. 1 shows a simplified block diagram of an ultrasound system, such as an echography system.

In the example considered, the system comprises a transducer 200. Generally, the transducer 200 may be any type of ultrasound transducers such as capacitive micromachined ultrasound transducers (cMUTS) or piezoelectric transducers.

The transducer 200 is connected to a signal generation circuitry 100 and an analysis circuitry 110. For example, the signal generation circuitry 100 may include a control circuit 102 and a so called "pulser" circuit 104 configured to generate a drive or transmission signal TX to be applied to the transducer 200. For example, the control circuit 102 may provide a control signal, which activates or deactivates the pulser circuit 104. The pulser circuit 104, when activated, may then apply to the transducer 200 via the transmission signal TX a voltage with a square or sinusoidal waveform.

Accordingly, when the pulser circuit 104 is activated, the transmission signal TX will be a periodic voltage signal with a given frequency and amplitude oscillating between a minimum voltage and a maximum voltage. For example, in case of echography systems, the frequency of the transmission signal TX is often between 1 and 2 MHz (Megahertz). Moreover, the transmission signal TX is often a high voltage drive signal, i.e., a signal wherein the maximum voltage is greater than 10 V, typically between 20 V and 200 V, and/or the minimum voltage is smaller than −10 V, typically between −20 V and −200 V. For example, the transmission signal TX often oscillates between 0 and +200 V, −200 V and 0 V, or −100 V and +100V.

Accordingly, when the pulser circuit 104 is activated, the transducer 200 will be stimulated and generate an ultrasound signal to be transmitted to a target object. Conversely, when the pulse circuit 104 is deactivated, the transducer 200 may be used to receive an ultrasound signal, i.e., an echo, reflected from the target object. For this reason, the transducer 200 should be placed in a high impedance state when the pulser circuit 104 is deactivated. This may be obtained by an appropriate configuration of the pulser circuit 104 or as shown in FIG. 1 by an optional transmit-and-receive (T/R) switch 120, which selects whether the transducer 200 is connected to the driver circuitry 100 or the analysis circuitry 110. For example, as shown in FIG. 1, the control circuit 102 may control for this purpose also the T/R switch 120.

Conversely, the analysis circuitry 110 is configured to analyze the received signal RX, i.e., the voltage at the transducer 200 when the pulser circuit 104 is deactivated. For example, the analysis circuitry 110 may comprise an amplifier circuit 112, such as a low noise amplifier (LNA), and a processing circuit 116 configured to analyze the amplified voltage at the transducer 200. Generally, the analysis circuitry 110 may comprise also other components, such as a filter and/or an analog-to-digital (A/D) converter 114 interposed between the amplifier circuit 112 and the processing circuit 116.

Generally, the signal generation circuitry 100 and the analysis circuitry 110 may be connected also to a user interface 130 comprising, e.g., display means and user input means.

FIG. 2 shows an example, in which a plurality of transducers 200 is used. For example, three transducers 200a, 200b and 200c are shown in FIG. 2. For example, the transducers 200 may be arranged in an array or matrix 20 comprising at least one row and a plurality of columns.

Generally, a respective pulser circuit 104 could be provided for each of the transducers 200a-200c. Conversely, in FIG. 2 is shown the case in which at least a subset of the transducers 200a-200c is driven by the same pulser circuit 104. In this case, the system comprises switching circuitry 30, such as a multiplexer, configured to connect, at a given time instant, the pulser circuit 14 to at least one (or possibly none) of the transducers 200a-200c. For example, the switching of the switching circuitry 30 may again be controlled by the signal generation circuitry 100, e.g., the control circuit 102.

For example, in case a single pulser circuit 14 is used for the complete array 20, the switching circuitry 30 may be a so called matrix switch, which permits a selection of the row and column of the array. Reference can be made for this purpose, e.g., to document US 2010/0152587 A1, which discloses various solutions for driving a plurality of transducers with one or more pulser circuits and which is incorporated herein by reference.

As shown in FIG. 3, the switching circuitry 30 may comprise, for example, one or more switches 300 configured to connect one or more transducers 200a-200c to a given signal generation circuitry 100, in particular a given pulser circuit 104. For example, in FIG. 3 are shown three switches 300a, 300b and 300c, wherein each of the switches 300a-300c is interposed between the pulser circuit 104 and a respective transducer 200a-200c.

The same applies also to the analysis circuitry 110, i.e., switching circuitry could be provided to connected one or more amplifiers 112 to respective subsets of transducers 200.

In this case, the target may be "scanned" by performing a series of measurements in which a focused ultrasonic wave is generated by a first group of transducers 200 and the reflected ultrasonic wave is received by a second group of transducers 200.

Accordingly, the switches 300a-300c of these switching circuitries 30 should support high voltages and currents, and high frequencies and slew-rates.

FIG. 4 shows in this respect a possible implementation of such a switch 300.

Specifically, in the example considered, the switch 300 comprises two terminals T1 and T2 being either connected together (closed) or disconnected (opened), and two control terminals SET and RESET for receiving control signals indicating whether the two terminals T1 and T2 should be electrically connected (conductive) or disconnected (non-conductive), respectively.

Specifically, in the example considered, the switch 300 is implemented with two Field Effect Transistors (FET) $SW_1$ and $SW_2$ connected back-to-back (source nodes shorted together) to allow for bipolar/bidirectional operation. For example, these transistors may be implemented as Double- Diffused MOS (Metal-Oxide-Semiconductor). Basically, this connection is preferable due to the parasitic body diodes (as shown in FIG. 4) which would provide a conduction path from source to drain during the positive or negative phase of the drive signal TX. Accordingly, in the example considered, the drain of the switch $SW_1$ is connected to the terminal T1, the drain of the switch $SW_2$ is connected to the terminal T2 and the sources of the switches $SW_1$ and $SW_2$ are connected (e.g., directly) to a common node S.

Also the gates of the transistors $SW_1$ and $SW_2$ are connected (e.g., directly) together at a common node G and controlled by a control circuit 310 as a function of the control signals provided at the terminals SET and RESET Specifically, the control circuit 310 should ensure that:

the gate-source voltage $V_{GS}$ of the transistors (i.e., the voltage between the nodes G and S) is greater than the threshold voltage of the transistors $SW_1$ and $SW_2$ when the control signal SET indicates that the switch 300 should be closed, and the gate-source voltage $V_{GS}$ of the transistors is smaller than the threshold voltage of the transistors $SW_1$ and $SW_2$ when the control signal RESET indicates that the switch 300 should be opened.

However, when the switch 300 is closed, the source voltage at the node S will be close to the drain voltage of the transistor $SW_1$, and the source voltage will thus follow the drive signal TX. Thus, in order to switch the switch 300 on, the node G should be connected to a high voltage, e.g., the maximum voltage of the drive signal TX.

Conversely, document US 2005/0146371 A1 discloses possible implementations of the control circuit 310 permitting that the control circuit 310 operates with low voltage signals, e.g., in the range between 0 V and 5 V.

Basically, this document proposes to change the state (on or off) of the switch 300 only when the terminal T1 is connected to ground GND.

Basically, as shown in FIG. 5, the circuit of document US 2005/0146371 A1 comprises a first circuit 312 configured to charge the node G when the switch 300 has to be closed (e.g., when the signal SET is high). Specifically, in document US 2005/0146371 A1 the circuit 312 comprises a switch (M4 in the cited document) configured to connect the node G to a low voltage source $V_{go}$ (e.g., 5 V), thereby charging the node G to approximately $V_{go}$, because the node S is connected to ground via the diode of the transistor $SW_1$.

The circuit comprises moreover a second circuit 314 configured to discharge the node G when the switch 300 has to be opened (e.g., when the signal RESET is high). Specifically, in document US 2005/0146371 A1 the circuit 314 comprises a gate clamp (M1 in the cited document) configured to short circuit the node G to the node S, thereby discharging the node G to approximately 0 V, because again the node S is connected to ground via the diode of the transistor $SW_1$.

Accordingly, in document US 2005/0146371 A1, the node G is charged to a low voltage compared to the maximum voltage of the drive signal TX. However, the parasitic gate-source capacitance $C_{GS}$ of the transistors $SW_1$ and $SW_2$ will retain this voltage. For this reason, once the gate-source voltage has stabilized (either 5 V or 0 V) the node G may be disconnected and the gate-source voltage $V_{GS}$ remains substantially constant, thereby maintaining the switch 300 closed/opened when the signal generation circuitry 100 drives the switch 300 and/or the voltage at the transducer 200 has to be provided to the analysis circuitry 110.

Unfortunately, leakage current may still discharge the node G. In this regards, document US 2005/0146371 A1 proposes to reprogram periodically the gate-source voltage $V_{GS}$.

Those of skill in the art will appreciate that such bipolar/bidirectional high-voltage switches 300 may also be used in other applications, such as for example liquid crystal displays (LCD) requiring high voltages (100 V)

BRIEF SUMMARY

The inventors have observed that the solutions disclosed in document US 2005/0146371 A1 may cause malfunctions. For example, the switches $SW_1$ and $SW_2$ comprise also a parasitic drain-gate capacitance, and accordingly, positive and negative transitions at the terminals T1 or T2 may increase or decrease the gate-source voltage, respectively. For this reason, a closed switch may be switched off after several oscillations of the signal DRV.

In view of the above, the present disclosure provides solutions which overcome one or more of the above drawbacks.

One or more embodiments of the present disclosure are directed to switching circuitry and a related method and integrated circuit.

The claims are an integral part of the technical teachings of the disclosure provided herein.

As mentioned in the foregoing, embodiments of the present disclosure relate to switching circuitry, e.g., integrated in an integrated circuit, adapted to be used, e.g., in an echography system or other high voltage applications.

In various embodiments, the switching circuitry comprises two transistors connected in series between two terminals, wherein the two transistors comprise a respective control terminal connected to a common control node. Accordingly, a capacitance, i.e., the gate-source capacitances of the transistors, is connected between the common control node and the intermediate node between the two transistors and the two transistors are rendered conductive or non-conductive as a function of the voltage at this capacitance.

In various embodiments, the switching circuitry comprises a control circuit comprising a first circuit configured to charge the capacitance as a function of a first control signal, and a second circuit configured to discharge the capacitance as a function of a second control signal.

For example, in various embodiments, the two transistors may be n-channel Field Effect Transistors (FET). In this case, the first control signal may indicate that the two transistors should be conductive and the second control signal may indicate that the two transistors should be non-conductive.

For example, in various embodiments, the first circuit may comprise two sub-circuits. The first sub-circuit is configured to selectively apply a first voltage to the common control node, and the second sub-circuit is configured to selectively apply a second voltage to the intermediate node, wherein the first voltage is greater than the second voltage, thereby generating a positive voltage at the capacitance.

Similarly, in various embodiments, the second circuit may comprise two sub-circuits. The first sub-circuit is configured to selectively apply a first voltage to the intermediate node and the second sub-circuit is configured to selectively apply a second voltage to the common control node, wherein the first voltage is equal to or greater than the second voltage, thereby generating a short-circuit or a negative voltage at the capacitance.

In various embodiments, the control circuit comprises moreover a third circuit. The third circuit comprises a plurality of diodes and at least one switch configured such that:
a) when the voltage at the capacitance is greater than a given threshold value, i.e., the threshold voltage of the transistors, two diodes are connected in cascade between the intermediate node and the common control node, thereby enabling current flow from the intermediate node to the common control node, and
b) when the voltage at the capacitance is smaller than the given threshold value, two diodes are connected in series between the common control node and the intermediate node, thereby enabling current flow from the common control node to the intermediate point.

In various embodiments, a parasitic and/or an appropriately designed capacitance is thus associated with the intermediate point between the two diodes connected in series between the common control node and the intermediate node between the two transistors.

Accordingly, once the switching circuit has been set or reset by means of the control signals, an oscillating signal may be applied to at least one of the two terminals of the switching circuit in order to recharge or further discharge the gate-source capacitances of the two transistors, i.e., the capacitance between the common control node and the intermediate node between the two transistors, thereby maintaining the state of the switching circuit.

Specifically, when the two transistors are conductive and a positive transition is applied to a terminal, charge will be transferred from the intermediate node to the parasitic capacitance, while a transfer of charge from the common control node to the parasitic capacitance is inhibited. Conversely, when a negative transition is applied to the terminal, charge will be transferred from the parasitic capacitance to the common control node, thereby recharging the gate-source capacitances of the two transistors.

Similarly, when the two transistors are non-conductive and a negative transition is applied to a terminal, charge will be transferred from the parasitic capacitance to the intermediate node between the two transistors, while a transfer of charge from the common control node to the parasitic capacitance is inhibited. Conversely, when a positive transition is applied to the terminal, charge will be transferred from the common control node to the parasitic capacitance, thereby discharging the gate-source capacitances of the two transistors.

For example, in various embodiments, the third circuit comprises two branches, each comprising two diodes connected in cascade. In this case, at least one switch may be used to selectively connect either the first branch or the second branch between the common control node and the intermediate node. In various embodiments, the at least one switch may be driven as a function of the voltage at the capacitance, i.e., the gate-source voltage of the two transistors.

For example, in various embodiments the at least one switch is implemented with two transistors. An n-channel FET is connected in series with the first branch between the intermediate node and the common control node, wherein the gate of the n-channel FET is connected to the common control node. Moreover, a p-channel FET is connected in series with the second branch between the common control node and the intermediate node, wherein the gate of the p-channel FET is connected to the common control node.

Instead, in other embodiments a single branch is used. For example, in various embodiments, a first and a second n-channel FET may be connected in series between the common control node and the intermediate node, and a first and a second p-channel FET may be connected in series between the common control node and the intermediate node. In this case, two diodes may be connected in cascade, wherein the anode of the first diode is connected to the intermediate point between the two n-channel FET and the cathode of the second diode is connected to the intermediate point between the two p-channel FET.

BRIEF DESCRIPTION OF THE SEVERAL VIEWS OF THE FIGURES

Embodiments of the present disclosure will now be described with reference to the annexed drawings, which are provided purely by way of non-limiting example and in which.

DETAILED DESCRIPTION

In the following description, numerous specific details are given to provide a thorough understanding of embodiments. The embodiments can be practiced without one or several specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The headings provided herein are for convenience only and do not interpret the scope or meaning of the embodiments.

In the following FIGS. 6 to 21 parts, elements or components which have already been described with reference to FIGS. 1 to 5 are denoted by the same references previously used in such Figures; the description of such previously described elements will not be repeated in the following in order not to overburden the present detailed description.

As mentioned in the foregoing, the present disclosure relates to a high voltage switching circuitry 400. For example, such switching circuitry 400 may be used in place of the switches 300 disclosed in the foregoing. Accordingly, the respective description will not be repeated again.

Figure 1:
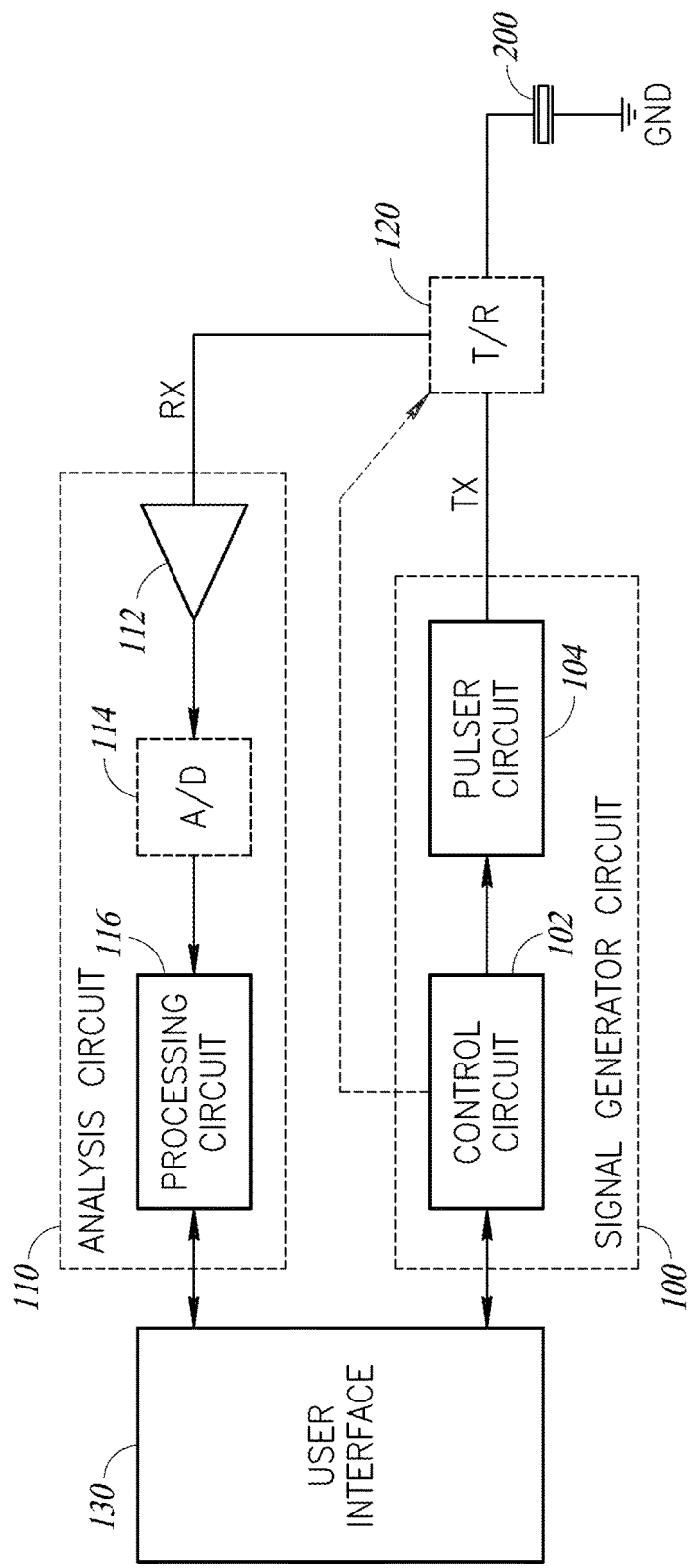
FIGS. 1, 2 and 3 shows examples of ultrasound systems.
Figure 2:
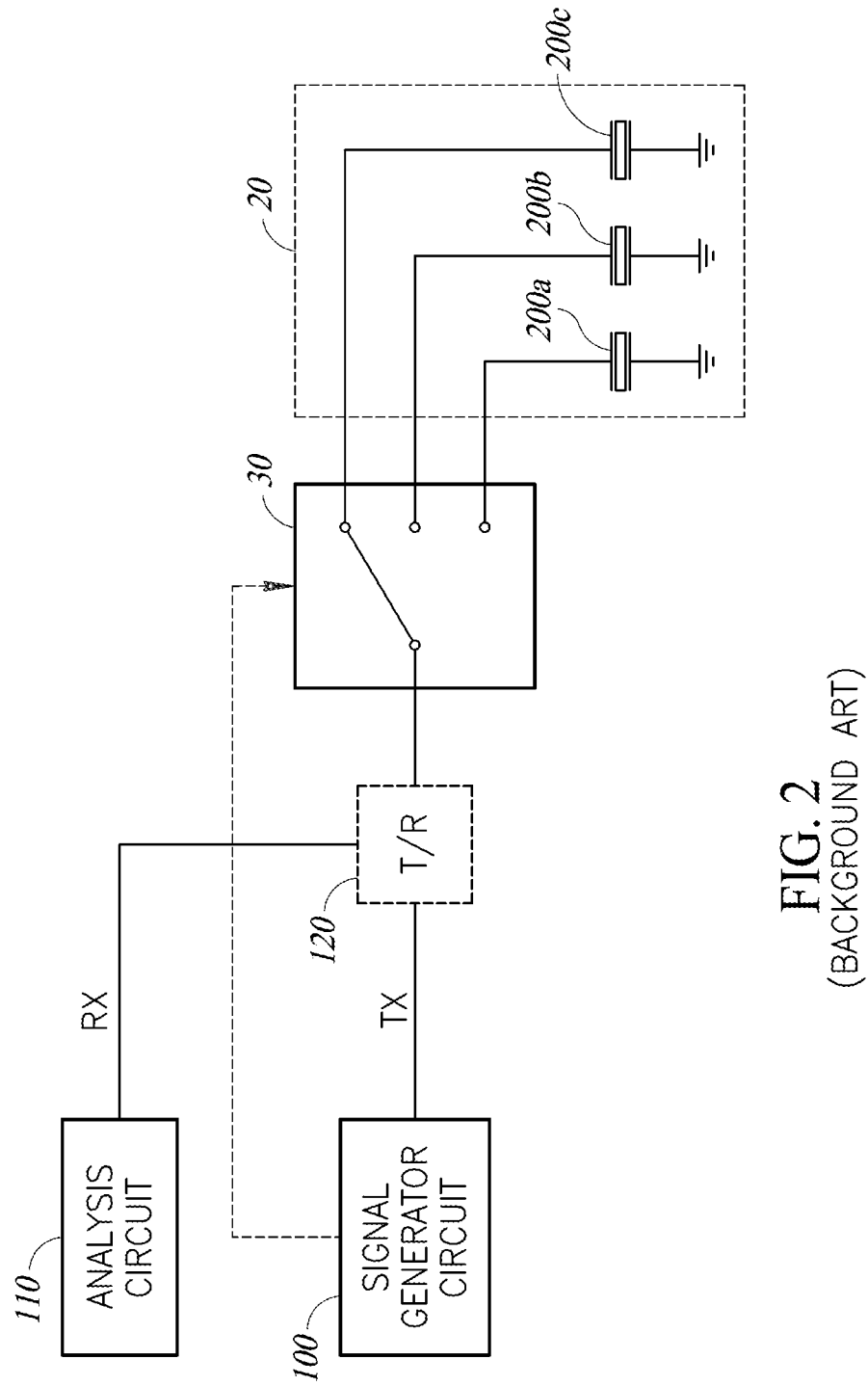
Figure 3:
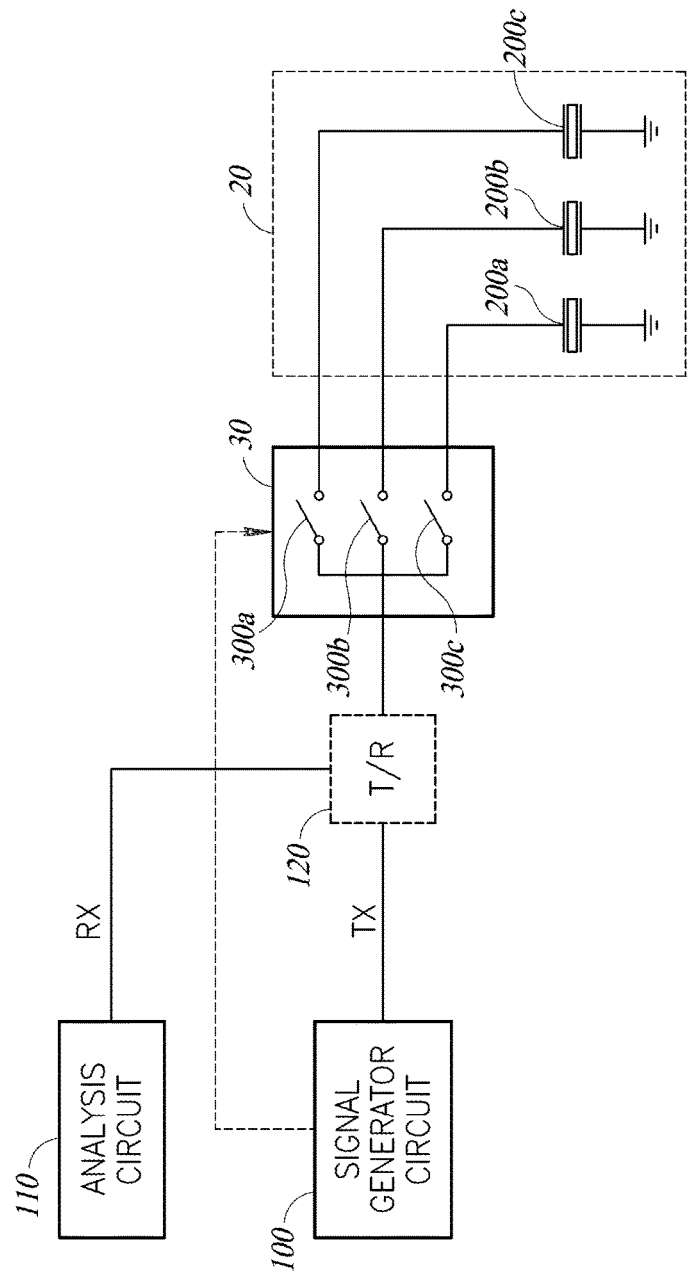
Figure 4:
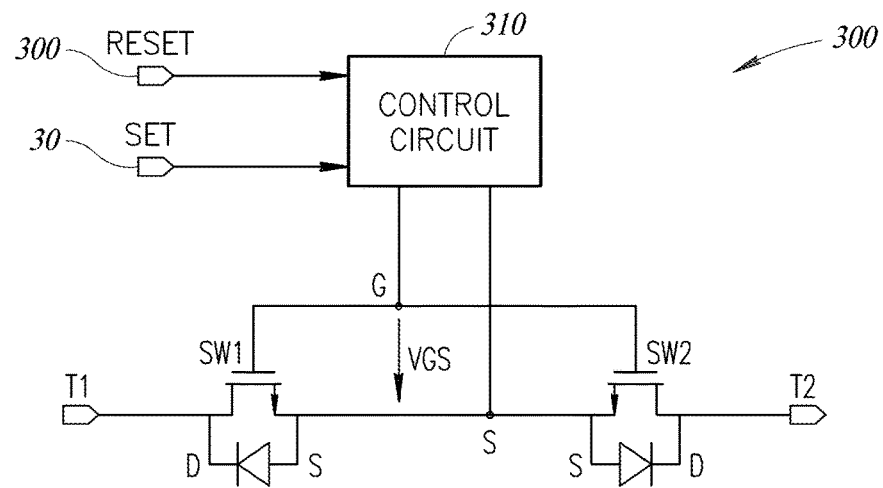
FIGS. 4 and 5 show examples of high voltage switching circuits adapted to be used in the systems of FIGS. 1 to 3.
Figure 5:
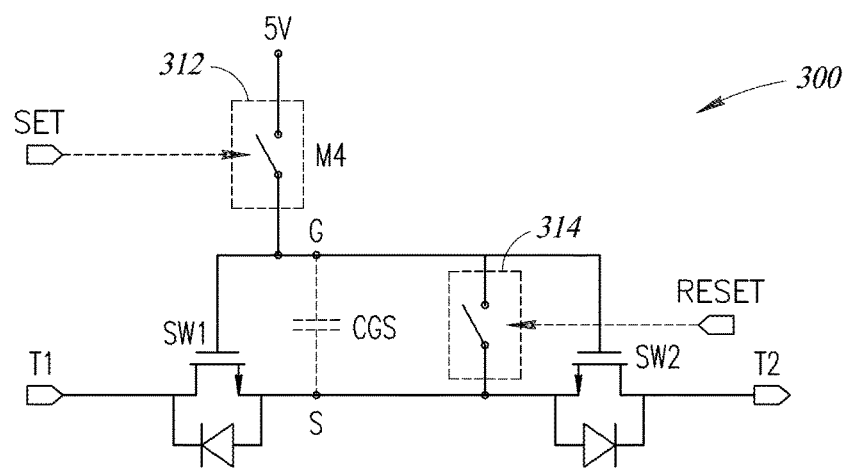
Figure 6:
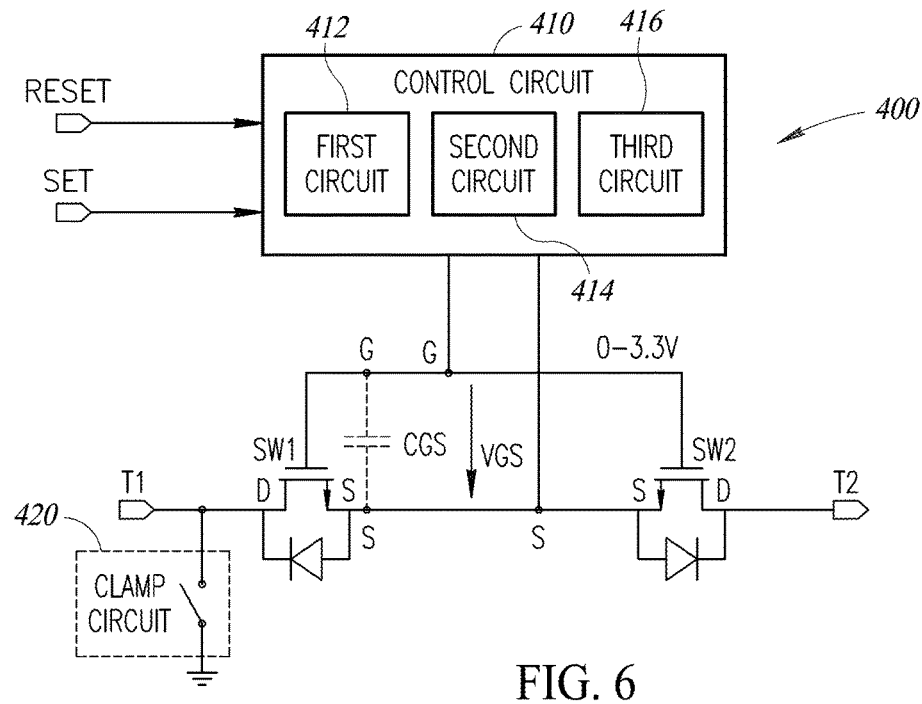
FIGS. 6 and 7 show embodiments of a control circuit for a high voltage switching circuit in accordance with embodiments of the present disclosure.

FIG. 6 shows a first embodiment of the switching circuitry 400.

Generally, also the switching circuitry 400 of the present disclosure comprises two terminals T1 and T2 being either connected together (closed/conductive condition) or disconnected (opened/non-conductive condition), and two control terminals SET and RESET for receiving control signals indicating whether the two terminals T1 and T2 should be connected together or disconnected, respectively.

Specifically, in the embodiment considered, the switch 400 is implemented with two n-channel FET (Field Effect Transistors) $SW_1$ and $SW_2$ connected back-to-back (source nodes shorted together) to allow for bipolar and bidirectional operation. For example, these transistors may be implemented as Double-Diffused MOS (DMOS). As mentioned in the foregoing, this connection is preferable due to the parasitic body diodes of the transistors $SW_1$ and $SW_2$.

Accordingly, in the embodiment considered, the drain of the switch $SW_1$ is connected (e.g., directly) to the terminal T1, the drain of the switch $SW_2$ is connected (e.g., directly) to the terminal T2 and the sources of the switches $SW_1$ and $SW_2$ are connected (e.g., directly) to a common node S. Also the gates of the transistors $SW_1$ and $SW_2$ are connected (e.g., directly) together at a common node G and controlled by a control circuit 410 as a function of the control signals provided at the terminal SET and RESET. Specifically, the control circuit 410 is configured to ensure that:

the gate-source voltage $V_{GS}$ of the transistors $SW_1$ and SW (i.e., the voltage between the node G and the node S) is greater than the threshold voltage of the transistors $SW_1$ and $SW_2$ when the control signal SET indicates that the switch 400 should be closed (e.g., when the signal SET is high), and the gate-source voltage $V_{GS}$ of the transistors $SW_1$ and SW is smaller than the threshold voltage of the transistors $SW_1$ and $SW_2$ when the control signal RESET indicates that the switch 400 should be opened (e.g., when the signal RESET is high).

Similar to document US 2005/0146371 A1, also the control circuit 410 of the present disclosure may operate with low voltage signals, e.g., in the range between 0 V and 5 V, preferably between 0 V and 3.3 V.

For this purpose, the state of the switch 400 should be changed only when the node S is connected (substantially) to ground GND and the drive signal TX is deactivated.

As mentioned in the foregoing, the node S may be connected to ground GND via the diode of the switch $SW_1$ when the node T1 is connected to ground GND. For example, as described in the foregoing, the terminal T1 may be connected to ground GND via the pulser circuit 104.

However, generally, when the drive signal TX is deactivated, the terminal T1 may also be in a high impedance state, i.e., floating. For example, the terminal T1 may be floating, e.g., by disconnecting the terminal T1 or connecting the terminal T1 to the analysis circuitry 110 via the T/R switch 120. In this case, the switching circuitry 400 may comprise a clamp circuit 420 configured to connect the terminal T1 to ground GND when the state of the switch 400 has to be changed, e.g., when the signal SET is high or the signal RESET is high. For example, such a clamp circuit 420 may comprise an electronic switch, such as an n-channel FET, connected between the terminal T1 and ground GND.

Figure 7:
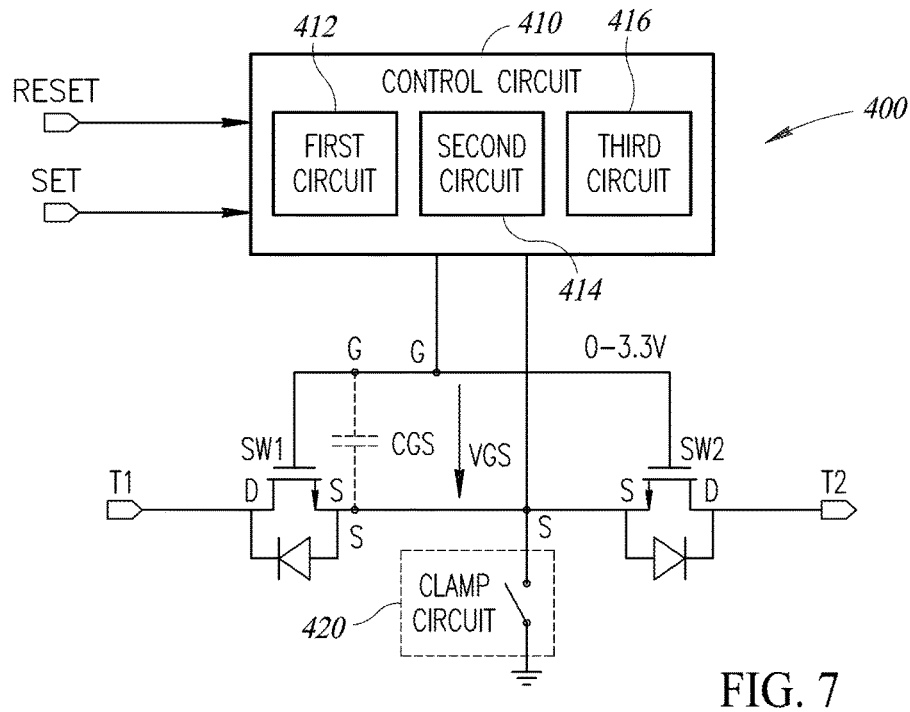

Conversely, FIG. 7 shows an embodiment in which a similar clamp circuit 422 is used to connect directly the node S to ground GND. For example, such a clamp circuit 422 may comprise an electronic switch, such as an n-channel FET, connected between the node S and ground GND. This embodiment may thus ensure that the node S is connected to ground GND, independently from fact whether the node T1 is connected to ground or floating.

In the embodiment considered, the control circuit 410 comprises three sub-circuits:

a first circuit 412 configured to charge the gate-source capacitance $C_{GS}$ between the node G and the node S when the signal SET indicates that the switch 400 has to be closed (e.g., when the signal SET is high), i.e., the transistors $SW_1$ and $SW_2$ have to be closed;

a second circuit 414 configured to discharge the gate-source capacitance $C_{GS}$ between the node G and the node S when the signal RESET indicates that the switch 400 has to be opened (e.g., the signal RESET is high), i.e., the transistors $SW_1$ and $SW_2$ have to be opened; and a third circuit 416 configured to maintain the state of the switch 400 when the signals SET and RESET indicates that the state of the switch 400 should be maintained (e.g., when the signals SET and RESET are low) and the drive signal TX is activated.

Figure 8:
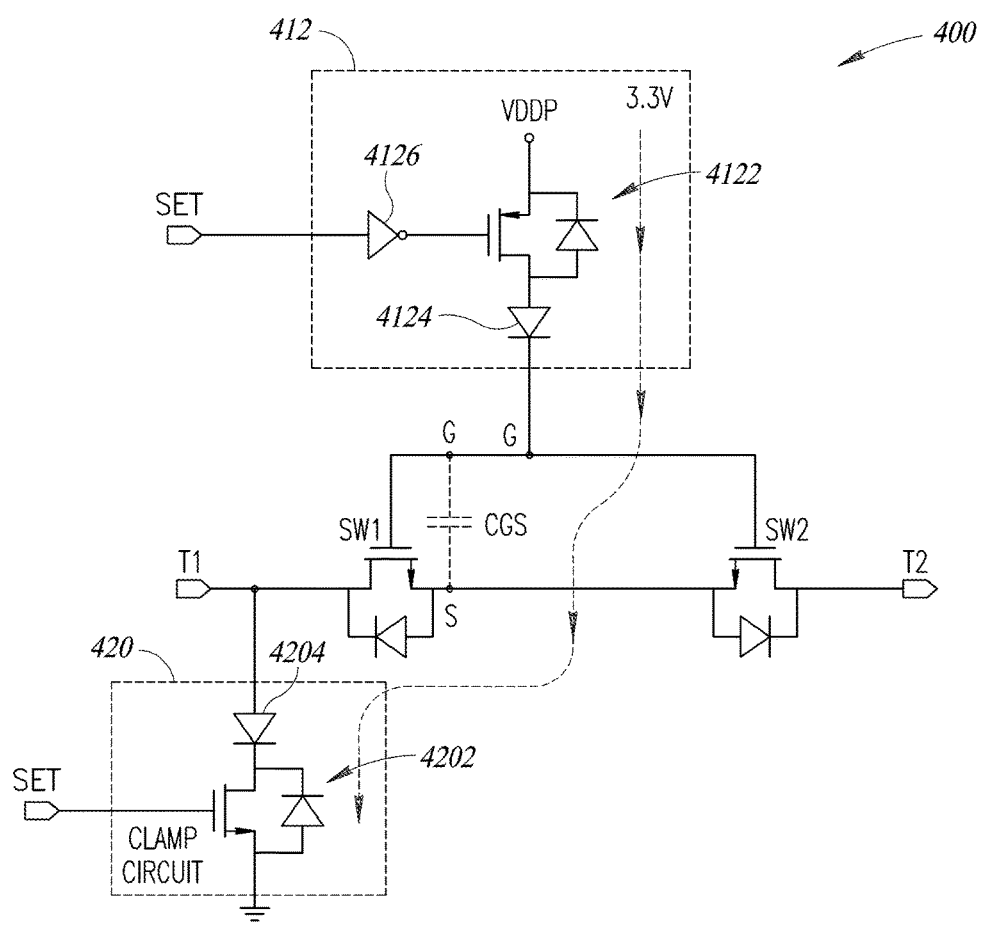
FIGS. 8 and 12 show embodiments of charge circuits adapted to switch on a high voltage switching circuit.

FIG. 8 shows a possible embodiment of the circuit 412.

Generally, as mentioned in the foregoing, the circuit 412 should charge the gate-source capacitance $C_{GS}$ when the signal SET indicates that the switch 400 has to be closed (e.g., when the signal SET is high).

Moreover, as mentioned in the foregoing, the external control circuit generating the signals SET and RESET (e.g., the control circuit 102) ensures that the signal SET tries to close the switch 400 when the drive signal TX applied to the terminal T1 is deactivated.

In the embodiment considered, in order to switch on the switch 400, at least one of the nodes T1, T2 and S should be connected to ground GND. As mentioned in the foregoing, this may be ensured directly by the signal generation circuitry 100 (e.g., the pulser circuit 104) and/or by a clamp circuit 420/422 in the switch 400 and/or a similar clamp circuit connected to the node T2.

For example, in the embodiment considered, a clamp circuit 420 is used. For example, in the embodiment considered, the clamp circuit 420 comprises an electronic switch 4202, such as an n-channel FET, and a diode 4204 connected in series between the terminal T1 and ground GND.

Specifically, in the embodiment considered, the source of the transistor 4202 is connected (e.g., directly) to ground GND, the drain of the transistor 4202 is connected (e.g., directly) to the cathode of the diode 4204, and the anode of the diode 4204 is connected (e.g., directly) to the terminal T1, i.e., the drain of the transistor $SW_1$. Accordingly, when a positive voltage is applied to the gate of the transistor 4202, the transistor 4202 will be closed, i.e., be conductive, and the terminal T1 will be short-circuited to ground GND. Conversely, the diode 4204 may be used to ensure that the body diode of the transistor 4202 is not rendered conductive when a negative voltage is applied to the terminal T1. This diode 4204 is purely optional, e.g., in case only positive voltages may be applied to the terminal T1.

In the embodiment considered, the switch 4202 is closed when the signal SET indicates that the switch 400 should be closed, e.g., when the signal SET is high.

In various embodiments, the diode 4204 is an active diode. Generally, an active diode means that the diode is implemented with an FET, wherein the body diode of the FET is used as the diode. In fact, in this case, the FET may be driven by a respective control signal. In this case, the FET behaves as a short circuit when the respective control signal has a first logic value, or as a diode when the control signal has a second logic value. For example, in the embodiment considered, such an FET could be driven with the signal SET in order to pull the node T1 to ground without the usual voltage drop of approximately 0.7 V at the diode 4204. Conversely, when the signal SET is low, the FET behaves exactly as the diode 4204 and blocks negative voltages at the node T1.

As mentioned in the foregoing, a similar clamp circuit may also be used for the clamp circuit 422 used to connect the node S to ground (see FIG. 7), e.g., by connecting (e.g., directly) the anode of the diode 4204 to the node S.

Accordingly, a low voltage, e.g., between 1.5 V and 5 V, e.g., 3.0 V or 3.3 V applied to the node G is sufficient to switch on the transistors $SW_1$ and $SW_2$.

For example, in the embodiment considered, the circuit 412 comprises for this reason an electronic switch 4122, such as a p-channel FET, and a diode 4124 connected in series between the node G and a positive supply voltage $VDD_P$, such as 3.3 V. Specifically, in the embodiment considered, the source of the transistor 4122 is connected (e.g., directly) to the supply voltage $VDD_P$, the drain of the transistor 4122 is connected (e.g., directly) to the anode of the diode 4124 and the cathode of the diode 4124 is connected (e.g., directly) to the node G. Accordingly, when a positive voltage is applied to the gate of the transistor 4122, the transistor 4122 will be opened and the node G will be floating. Conversely, the node G will be connected to the supply voltage $VDD_P$ and, thanks to the connection of the node S to ground, the node G will be charged, e.g., substantially to $VDD_P$ (neglecting the diode 4124). In fact, preferably, also the diode 4124 is an active diode driven as a function of the signal SET, i.e., the diode 4124 behaves as a short circuit, when the signal SET indicates that the switch 400 should be closed.

Accordingly, in the embodiment considered, the switch 4122 should be closed when the signal SET indicates that the switch 400 should be closed (e.g., when the signal SET is high). For example, considering the exemplary logic values of the signal SET and the opposed operation of the p-channel FET, the gate of the transistor 4122 may be driven by means of an inverted version of the signal SET. For example, in the embodiment considered, an inverter 4126 is interposed between the terminal SET and the gate of the transistor 4122.

Figure 9:
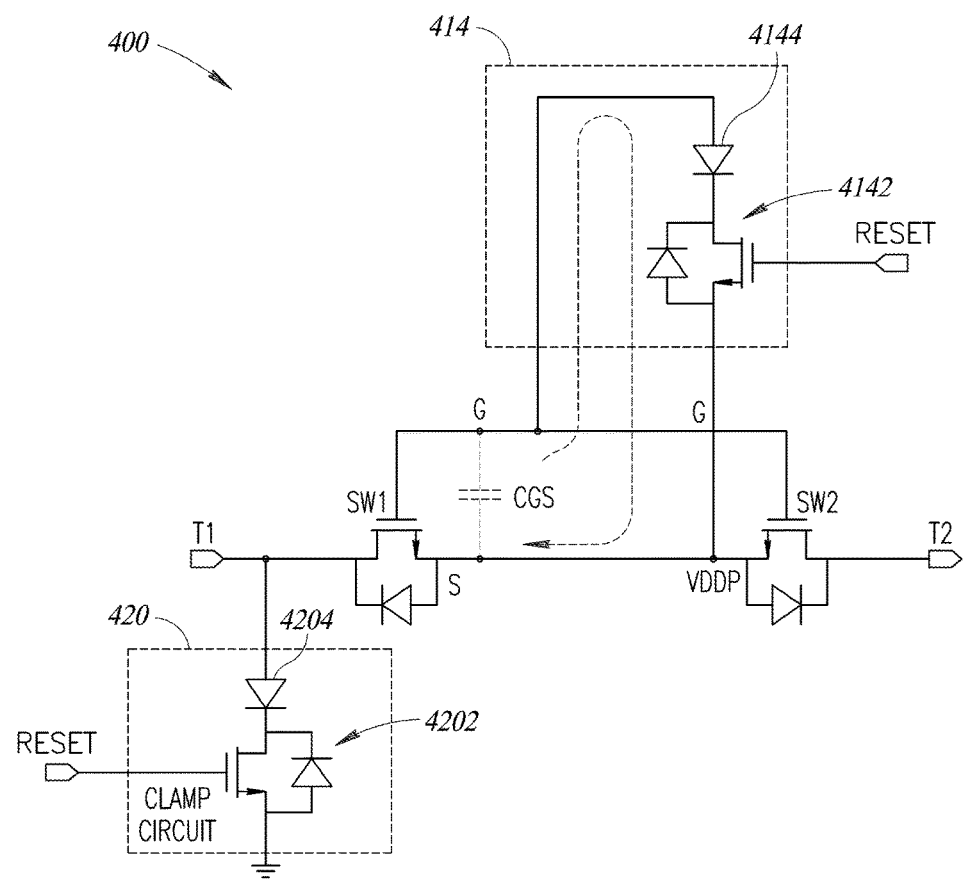
FIGS. 9, 10 and 11 show embodiments of discharge circuits adapted to switch off a high voltage switching circuit.

Conversely, FIG. 9 shows an embodiment of the circuit 414 configured to discharge the node G, when the signal RESET indicates that the switch 400 should be opened (e.g., when the signal RESET is high).

Again, as mentioned in the foregoing, the external control circuit generating the signals SET and RESET ensures that the signal RESET tries to close the switch 400 when the drive signal TX applied to the node T1 is deactivated.

In the embodiment considered, in order to switch off the switch 400, the node T1 and/or the node S should be connected to ground GND. As mentioned in the foregoing, this may be ensured directly by the signal generation circuitry 100 and/or by a clamp circuit 420/422 in the switch 400.

For example, in FIG. 9 is used the same clamp circuit 420 already shown in FIG. 8. However, in this case, the clamp circuit 420 should also be active when the signal RESET indicates that the switch 400 should be opened. Accordingly, the gate of the transistor 4222 could be driven, e.g., via an OR gate receiving at input the signals SET and RESET.

In the embodiment considered, the circuit 414 used to discharge the node G is implemented with a clamp circuit comprising an electronic switch 4142, such as an n-channel FET, and a diode 4144, preferably an active diode driven by means of the signal RESET, connected in series between the node G and the node S. Specifically, in the embodiment considered, the source of the transistor 4142 is connected (e.g., directly) to the node S, the drain of the transistor 4142 is connected (e.g., directly) to the cathode of the diode 4144 and the anode of the diode 4144 is connected (e.g., directly) to the node G. Accordingly, when a positive voltage is applied to the gate of the transistor 4142, the transistor 4142 will be closed and the node G is connected to the node S. For example, considering the exemplary logic levels of the signal RESET, the gate of the transistor 4142 may be driven directly by the signal RESET.

Accordingly, when a positive voltage is applied to the gate of the transistor 4142, the transistor 4142 will be closed and the node G will be connected to the node S and the node G will be discharged. Considering the connection of the node S to ground, the node G will thus be discharged to substantially 0 V (again neglecting the diode 4144, which preferably is an active diode).

The inventors have observed that this voltage level might not be sufficient, because charge injected into the node G may still increase the gate-source voltage $V_{GS}$ above the threshold voltage of the transistors $SW_1$ and $SW_2$, thereby closing the switch 400.

Figure 10:
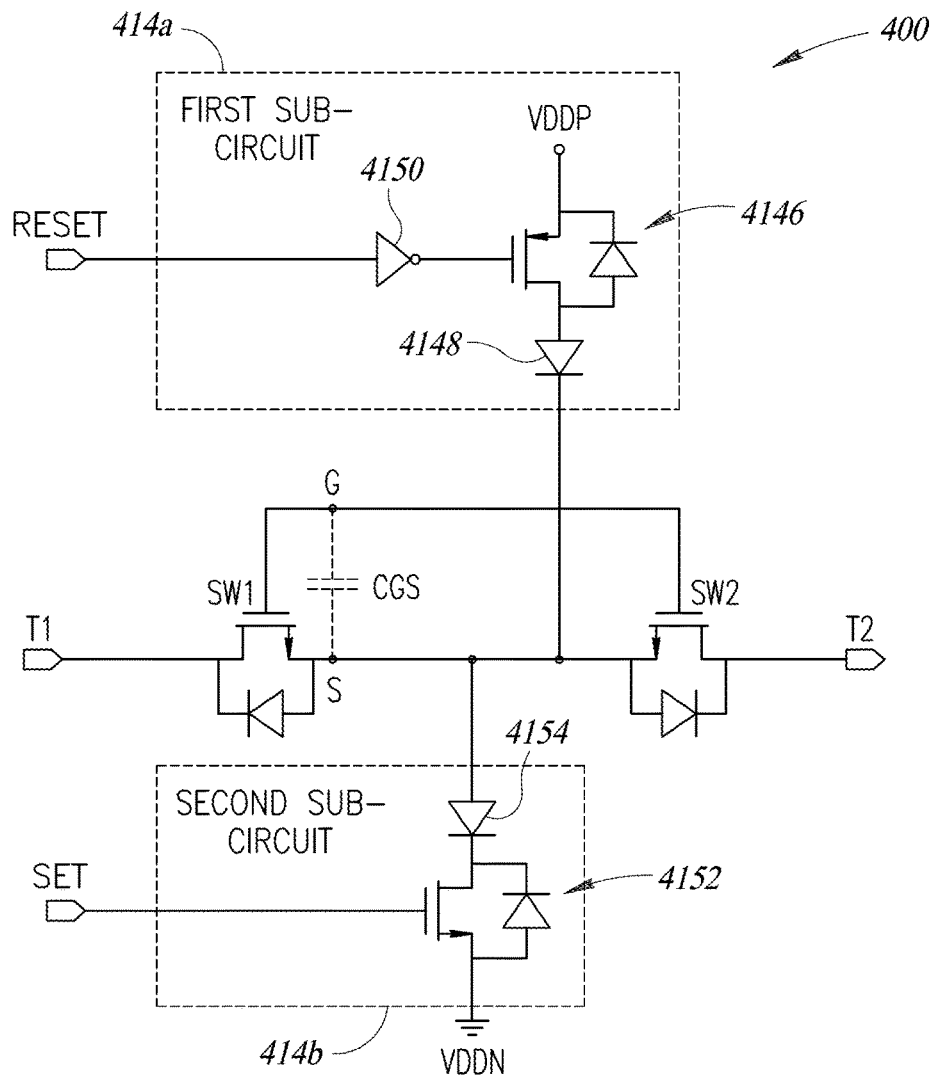

FIG. 10 shows in this regards an alternative embodiment of the circuit 414, in which a negative gate-source voltage $V_{GS}$ is created.

In the embodiment considered, the circuit 414 comprises two sub-circuits 414a and 414b.

Specifically, the first sub-circuit 414a is configured to apply a positive voltage to the node S when the signal RESET indicates that the switch 400 should be opened. For example, in the embodiment considered, the circuit 414a has the same architecture as the circuit 412 described with respect to FIG. 8, with the only difference that the circuit is connected to the node S and not the node G. Specifically, in the embodiment considered, an electronic switch 4146, such as a p-channel FET, and a diode 4148, preferably an active diode driven by means of the signal RESET, are connected in series between a positive supply voltage, e.g., $VDD_P$, and the node S, wherein the gate of the transistor 4146 is driven as a function of the signal RESET. For example, in the embodiment considered, an inverter 4150 is used to generate the drive signal applied to the gate of the transistor 4146, i.e., the supply voltage $VDD_P$ is applied to the node S when the signal RESET is high.

Conversely, a second circuit 414b is used to connect the node G to ground when the signal RESET indicates that the switch 400 should be opened. For example, in the embodiment considered, the circuit 414a has the same architecture as the clamp circuit 420 described with respect to FIG. 8, with the only difference that the circuit is connected to the node G and not the terminal T1. Specifically, in the embodiment considered, an electronic switch 4152, such as an n-channel FET, and a diode 4154, preferably an active diode driven by means of the signal RESET, are connected between the node G and ground GND, wherein the gate of the transistor 4152 is driven as a function of the signal RESET. For example, in the embodiment considered, the signal RESET is applied directly to the gate of the transistor 4152, i.e., the node G is connected to ground when the signal RESET is high.

Accordingly, in this embodiment, a negative gate-source voltage $V_{GS}$ (approximately $-VDD_P$) will be generated when the signal RESET indicates that the switch 400 should be opened.

Figure 11:
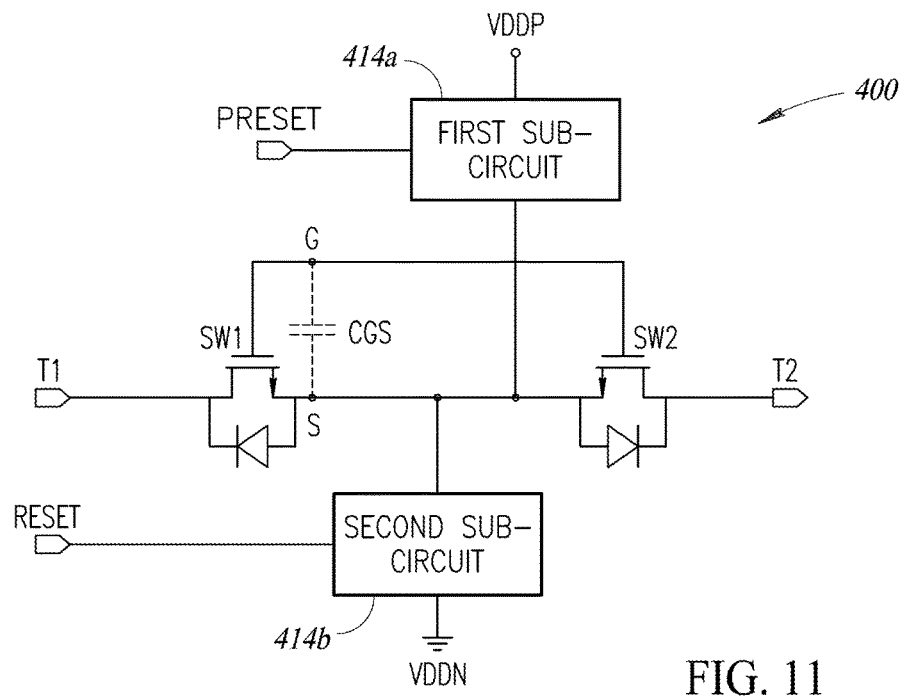

As shown in FIG. 11, generally, the circuit 414 may thus comprise two-sub-circuits:
- a first sub-circuit 414a configured to selectively apply a first voltage $VDD_P$ to the node S when the signal RESET indicates that the switch 400 should be opened; and
- a second sub-circuit 414b configured to selectively apply a second voltage $VDD_N$ to the node G when the signal RESET indicates that the switch 400 should be opened.

In the embodiment shown in FIG. 9, the voltages $VDD_P$ and $VDD_N$ are the same and the gate-source voltage is 0 V.

Conversely, in the embodiment shown in FIG. 10, the voltage $VDD_P$ is greater than the voltage $VDD_N$, thereby generating a negative gate-source voltage:

$$V_{GS} = VDD_N - VDD_P.$$

Figure 12:
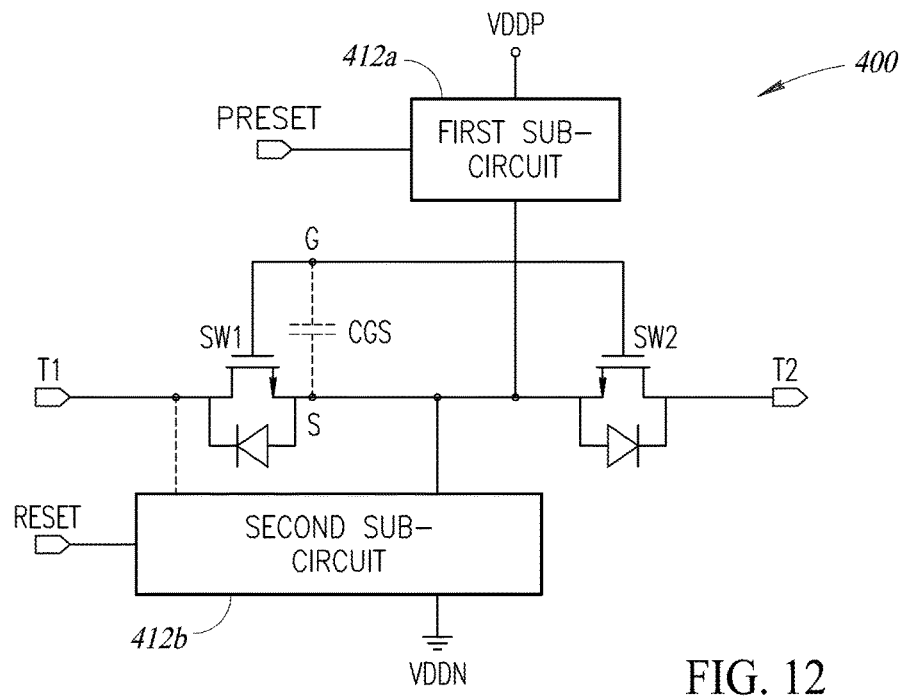

Generally, as shown in FIG. 12, the opposed behavior may be used for the circuit 412, i.e., the circuit 412 may thus comprise two-sub-circuits:
- a first sub-circuit 412a configured to selectively apply a first voltage $VDD_P$ to the node G when the signal SET indicates that the switch 400 should be closed; and
- a second sub-circuit 412b configured to selectively apply a second voltage $VDD_N$ to the node S when the signal SET indicates that the switch 400 should be closed.

Specifically, the second sub-circuit 412b may apply the second voltage $VDD_N$ to the node S:
- directly, as shown, e.g., with respect to the clamp circuit 422 (representing the circuit 412b in FIG. 7), or
- indirectly via the terminal T1 (or T2), as shown, e.g., with respect to the clamp circuit 420 (representing the circuit 412b in FIGS. 6 and 8)

Generally, the voltage $VDD_P$ should be greater than the voltage $VDD_N$, thereby generating a positive gate-source voltage:

$$V_{GS} = VDD_P - VDD_N.$$

For example, in the embodiment shown in FIGS. 6, 7 and 8, the voltage $VDD_N$ corresponds indeed to ground GND and $V_{GS} = VDD_P$.

Generally, the circuits 412 and 414 may also operate with different voltages $VDD_P$ and $VDD_N$.

Accordingly, in the previous embodiments, the circuit 412 charges the gate-source capacitance $C_{GS}$ and generates a positive gate-source voltage $V_{GS}$ when the signal SET has a first logic value (e.g., high) indicating that the switch 400 has to be closed. Conversely, the circuit 414 discharges the gate-source capacitance $C_{GS}$ and generates a negative gate-source voltage $V_{GS}$ when the signal RESET has a first logic value (e.g., high) indicating that the switch 400 has to be opened.

Accordingly, the gate-source voltage $V_{GS}$ may have two levels:
- a positive voltage (switch 400 closed), or
- either a zero voltage or preferably a negative voltage (switch 400 opened)

Finally, the node G is disconnected, i.e., not connected to a supply voltage, when the signals SET and RESET have a second logic values (e.g., both low).

Accordingly, when the signals SET and RESET have the second logic values (e.g., low) the gate-source capacitance will be discharged due to leakage and/or charge sharing with parasitic capacitance. Moreover, positive and negative charge may be injected into the gate node G through the gate-drain capacitances of the switches $SW_1$ and $SW_2$.

Accordingly, in several embodiments, the circuit 410 comprises also a rectification circuit 416 configured to inject charge into the gate node G in order to maintain the state of the switch 400 thanks to the oscillation at the node T1 and/or T2.

Figure 13:
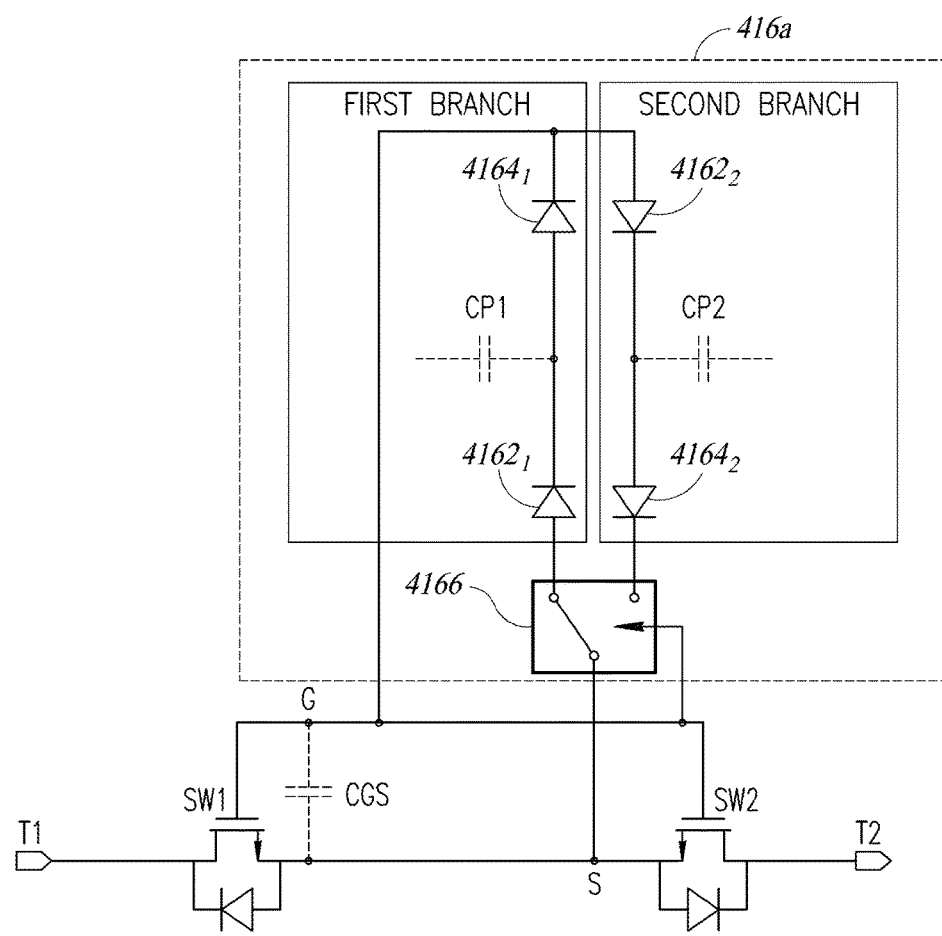
FIGS. 13, 14a, 14b, 15a and 15b show a first embodiment of a rectification circuit adapted to maintain the state of a high voltage switching circuit.

FIG. 13 shows in this respect a first embodiment of a rectification circuit 416a.

Specifically, in the embodiment considered, the rectification circuit 416a comprises two branches and an electronic switch 4166 configured to connect one of the branches between the nodes G and S.

Specifically, each of the branches comprises two diodes connected in series, i.e., diodes $4162_1$ and $4164_1$ for the first branch and diodes $4162_2$ and $4164_2$ for the second branch.

Generally, also a series connection of a more diodes may be used for the diodes 4162 and 4164.

More specifically, in the embodiment considered, the cathode of the diode $4164_1$ is connected (e.g., directly) to the node G, the anode of the diode $4164_1$ is connected (e.g., directly) to the cathode of the diode $4162_1$ and the anode of the diode $4164_1$ is connected to the switch 4166 and may thus be connected selectively to the node S. Conversely, the anode of the diode $4162_2$ is connected (e.g., directly) to the node G, the cathode of the diode $4162_2$ is connected (e.g., directly) to the anode of the diode $4164_2$ and the cathode of the diode $4164_2$ is connected to the switch 4166 and may thus be connected selectively to the node S.

Accordingly, the first branch defines a conductive path from the node S to the node G (with the opposite direction being blocked, i.e., non-conductive) and the second branch defines a conductive path from the node G to the node S (with the opposite direction being blocked), wherein one of the branches may be activated selectively via the switch 4166.

Moreover, in the embodiment considered, the switch 4166 is driven as a function of the state of the switch 400 (on/off), for example as a function of the signals SET/RESET or the gate-source voltage $V_{GS}$:
- when the switch 400 is closed (high gate-source voltage $V_{GS}$) the diodes $4162_1$ and $4164_1$ are connected between the nodes G and S; and
- when the switch 400 is opened (low gate-source voltage $V_{GS}$) the diodes $4162_2$ and $4164_2$ are connected between the nodes S and G.

Generally, a parasitic capacitance $C_{P1}$ will be associated with the node between the diodes $4162_1$ and $4164_1$ and a parasitic capacitance $C_{P2}$ will be associated with the node between the diodes $4162_2$ and $4164_2$. Preferably, these capacitances are increased voluntarily during the design process of the switch 400 and may be, e.g., between 100 fF (Femto-Farad) and several pF (Pico-Farad).

Figure 14A:
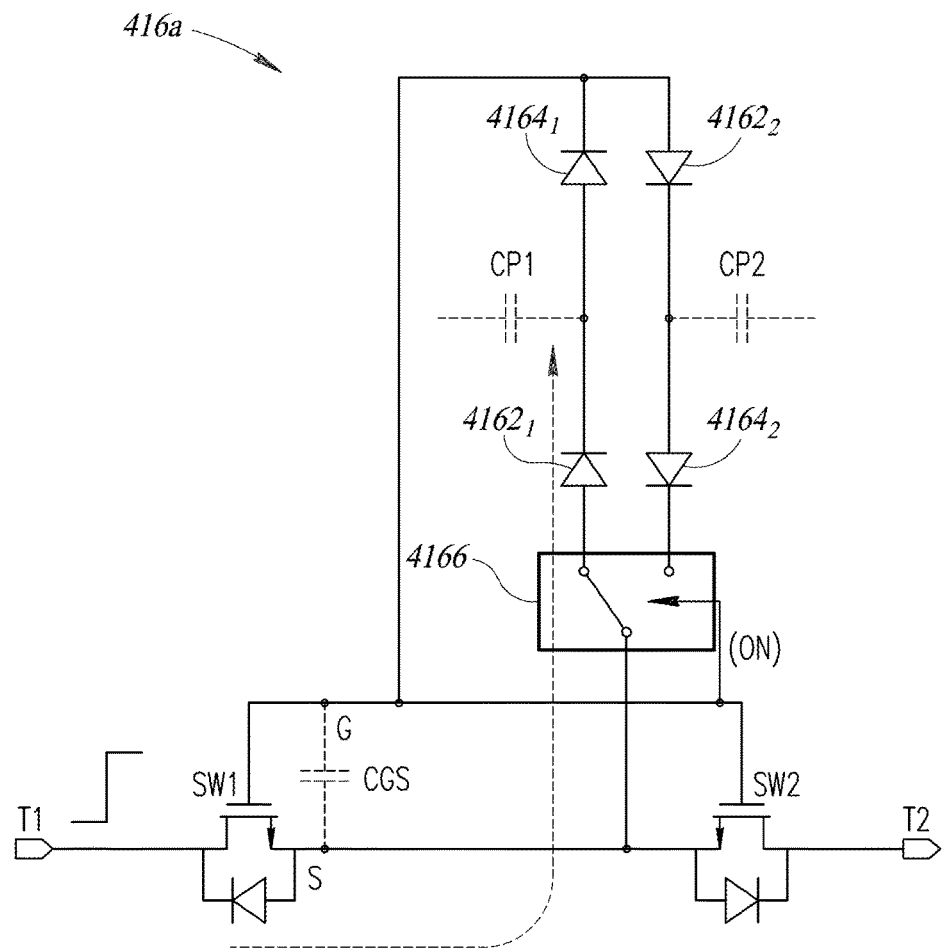

Accordingly, as shown in FIG. 14a, when the switch 400 is closed (ON), positive transitions at the terminal T1 (or T2) may be partially transferred through the diode $4162_1$ to the capacitance $C_{P1}$, thereby charging the capacitance $C_{P1}$ approximately to the voltage at the node T1. For example, assuming a forward voltage of 0.7 V for the diode $4162_1$, the capacitance $C_{P1}$ will be charged to approximately 99.3 V for a maximum voltage of 100 V at the node T1. Conversely, the node G will have a higher voltage, e.g., 103.3 V, because the gate-source capacitance $C_{GS}$ maintains the voltage difference. Accordingly, the diode $4164_1$ blocks a discharging of the node G to the capacitance $C_{P1}$ during this phase. Moreover, also the second branch comprising the diodes $4162_2$ and $4164_2$ is disconnected via the switch 4166.

Figure 14B:
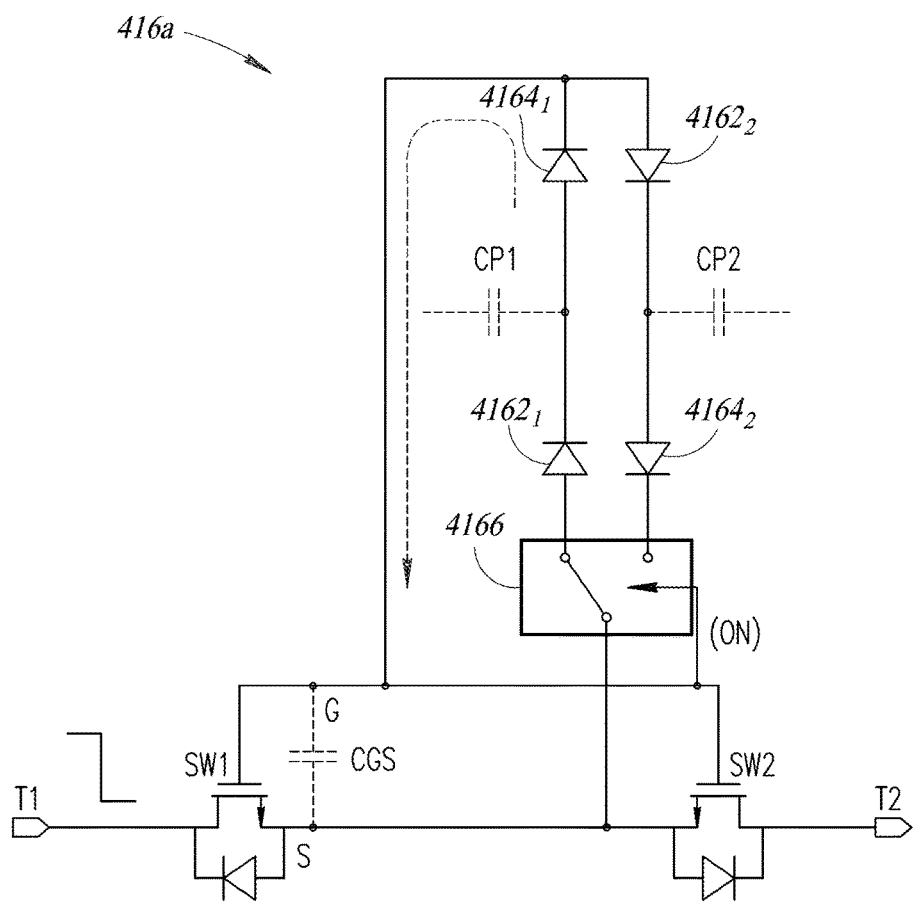

Conversely, as shown in FIG. 14b, when a negative transition occurs, the voltage at the node G will decrease. For example, assuming a minimum voltage of 0 V at the node T1, the voltage at the node G would decrease, e.g., to 3.3 V. Accordingly, the diode $4164_1$ will become conductive and the charge at the capacitance $C_{P1}$ will be transferred in part to the node G, thereby charging the gate-source capacitance $C_{GS}$.

Figure 15A:
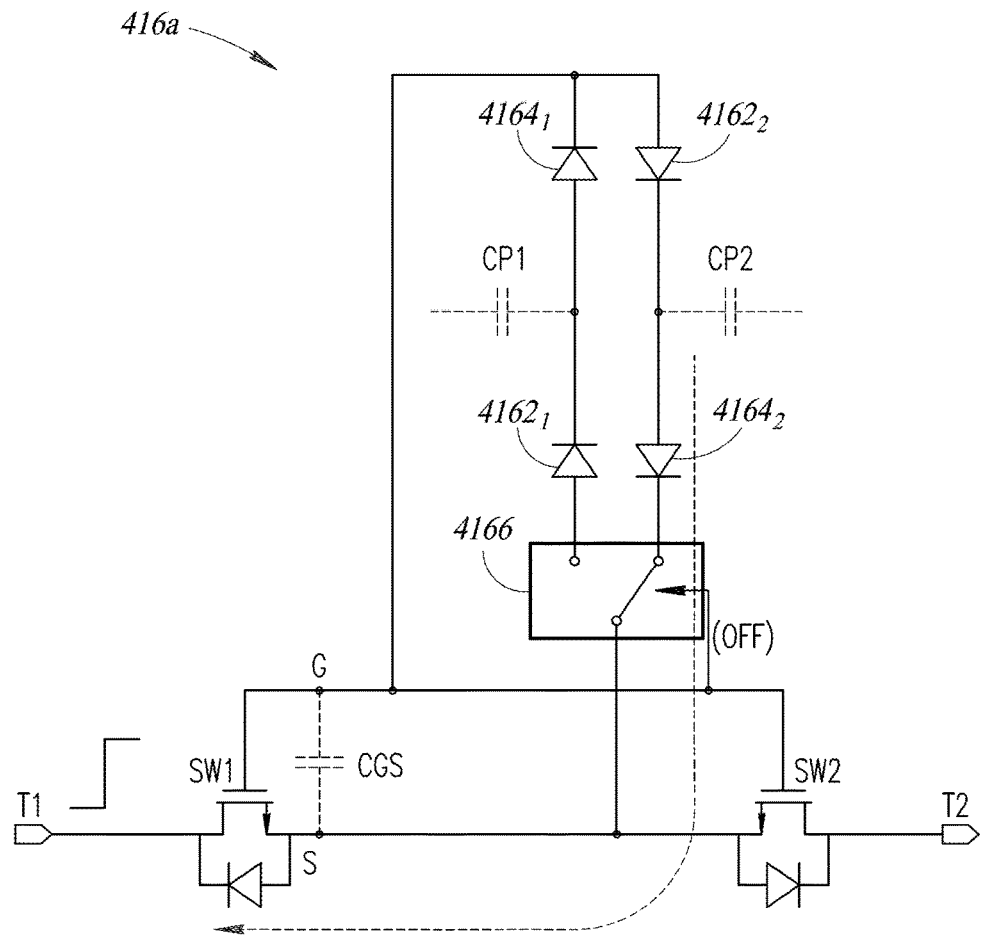
Figure 15B:
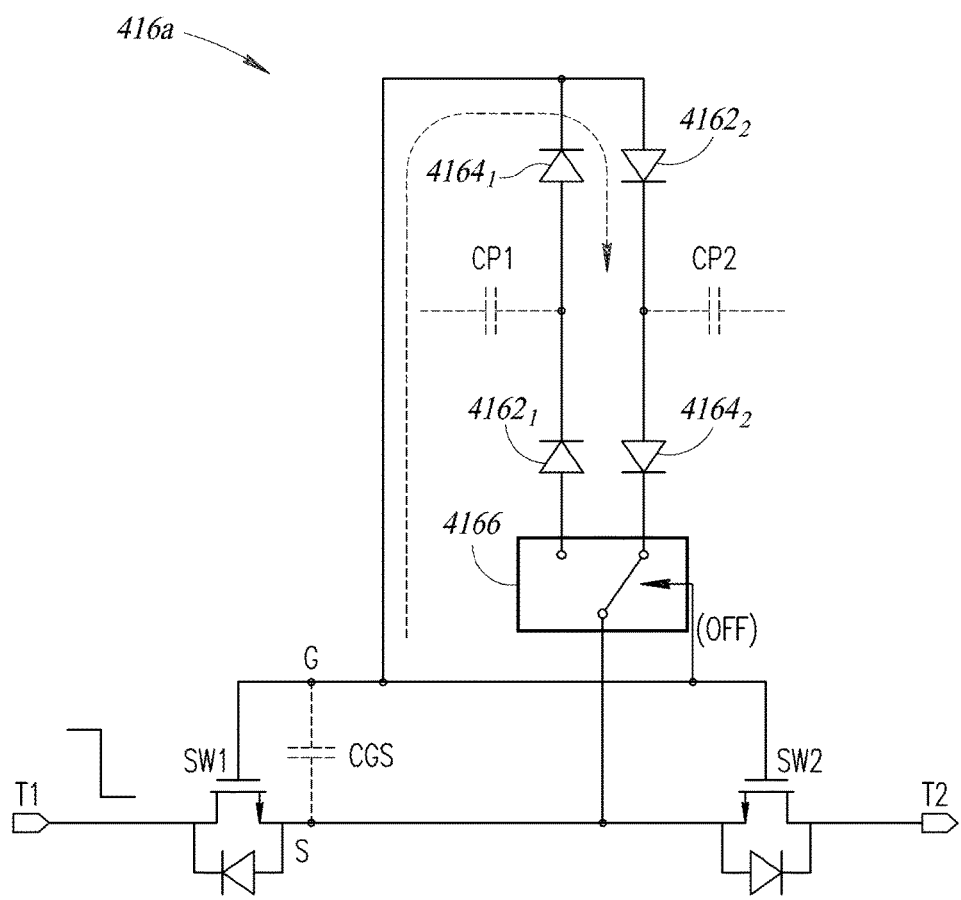

Conversely, as shown in FIGS. 15a and 15b the opposite behavior may be used to discharge the gate-source capacitance $C_{GS}$ via the second branch, i.e., the diodes $4162_2$ and $4164_2$, when the switch 400 is opened (OFF).

Specifically, as shown in FIG. 15a, when the switch 400 is opened (OFF), negative transitions at the terminal T1 may be used to discharge the capacitance $C_{P2}$ through the diode $4164_2$.

Conversely, as shown in FIG. 15b, when a positive transition occurs, the voltage at the node G will increase and the diode $4162_2$ will become conductive, thereby discharging the gate-source capacitance $C_{GS}$ to the capacitance $C_{P2}$.

Figure 16:
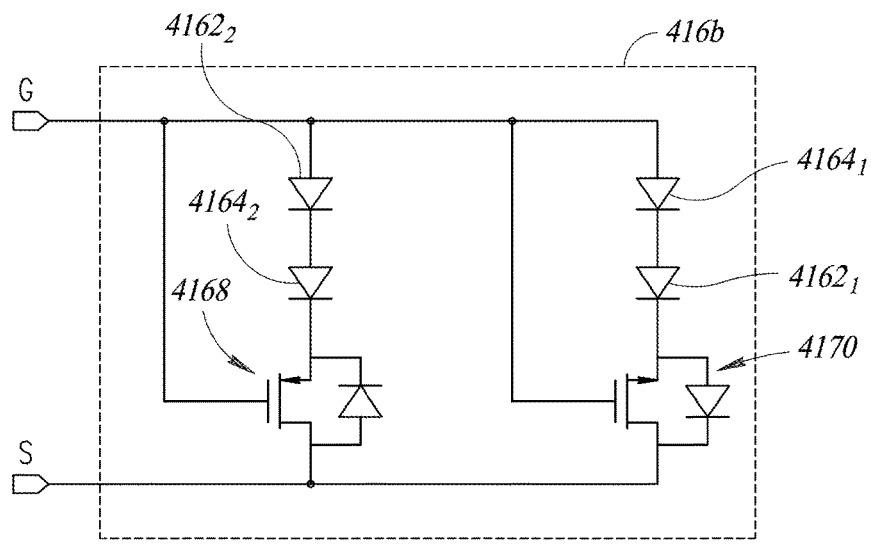
FIGS. 16, 17a and 17b show a second embodiment of a rectification circuit adapted to maintain the state of a high voltage switching circuit.
Figure 17A:
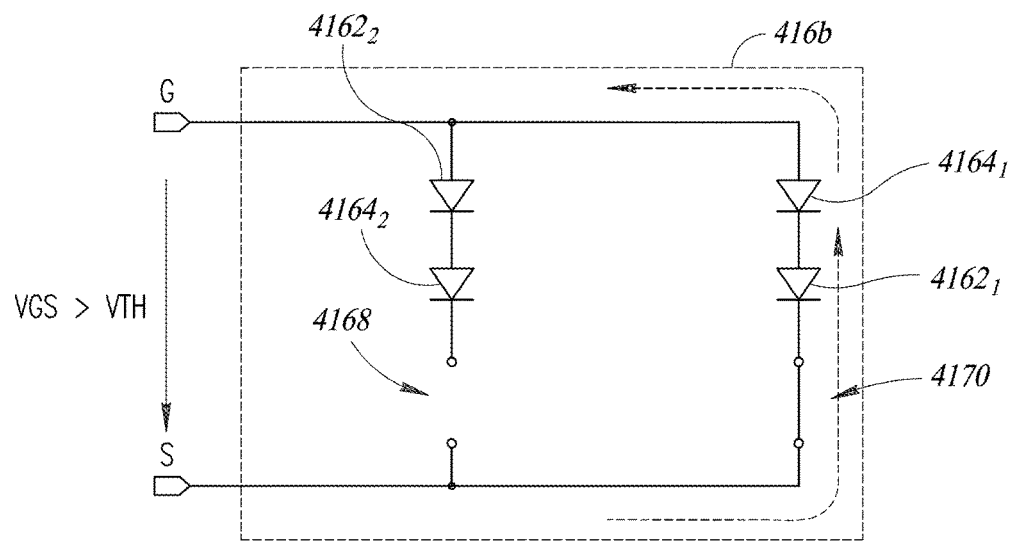
Figure 17B:
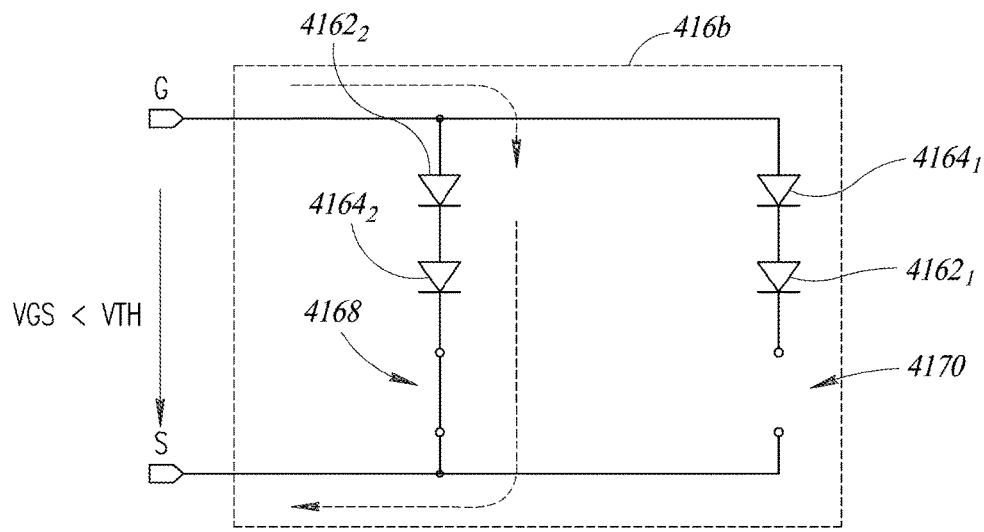

FIG. 16 shows a second embodiment of a rectification circuit 416b, wherein the switch 4166 is implemented with two FET 4168 and 4170.

Specifically, in the embodiment considered, the diodes $4162_2$/$4164_2$ and a p-channel FET 4168 are connected in series between the node G and the node S, and the diodes $4162_1$/$4164_1$ and an n-channel FET 4170 are connected in series between the node S and the node G.

Specifically, in the embodiment considered, the anode of the diode $4162_2$ is connected to the node G, the cathode of the diode $4162_2$ is connected to the anode of the diode $4164_2$ and the p-channel FET 4168 is used to connect selectively the cathode of the diode $4164_2$ to the node S. In the embodiment considered, the gate of the transistor 4168 is connected to the node G.

Conversely, the cathode of the diode $4164_1$ is connected to the node G, the anode of the diode $4164_1$ is connected to the cathode of the diode $4162_1$ and the n-channel FET 4170 is used to connect selectively the anode of the diode $4162_1$ to the node S. In the embodiment considered, the gate of the transistor 4170 is connected to the node G. For simplicity, the capacitances $C_{P1}$ and $C_{P2}$ are omitted in the figures.

Accordingly, also in this case, the diodes $4162_1$/$4164_1$ and $4162_2$/$4164_2$, respectively, represent two opposite conductive paths which may be enabled selectively.

Accordingly, when the gate-source voltage $V_{GS}$ is greater than the threshold voltage $V_{TH}$ of the transistors 4168 and 4170 (see FIG. 17a), the transistor 4168 is opened and the transistor 4170 is closed, i.e., only the diodes $4162_1$ and $4164_1$ are connected between the node S and the node G, thereby permitting only a charging of the node G. Conversely, when the gate-source voltage $V_{GS}$ is smaller than the threshold voltage $V_{TH}$ of the transistors 4168 and 4170 (see FIG. 17b), the transistor 4168 is closed and the transistor 4170 is opened, i.e., only the diodes $4162_2$ and $4164_2$ are connected between the node G and the node S, thereby permitting only a discharging of the node G.

Figure 18:
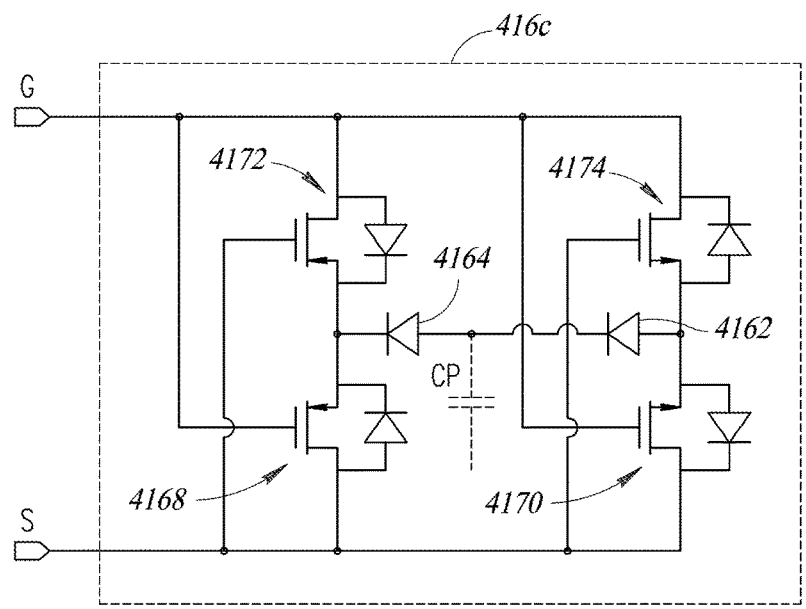
FIGS. 18, 19a and 19b show a third embodiment of a rectification circuit adapted to maintain the state of a high voltage switching circuit.
Figure 19A:
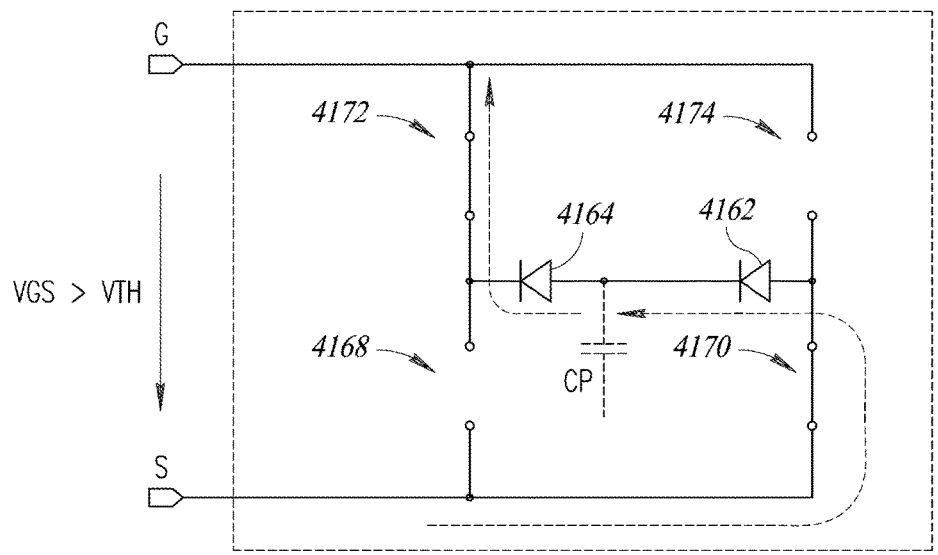
Figure 19B:
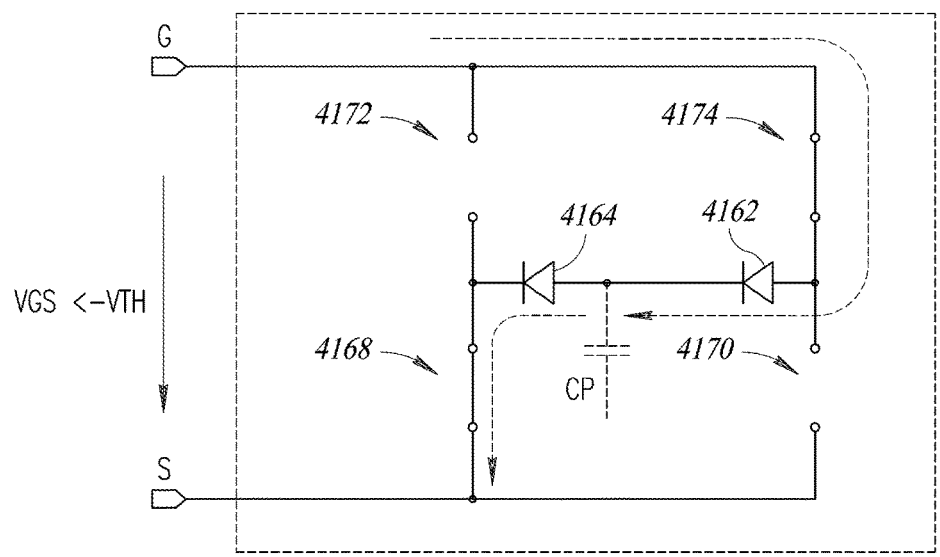

FIG. 18 shows a further embodiment of a rectification circuit 416c.

Specifically, in the embodiment considered, the rectification circuit 416c comprises a single branch comprising two (or more) diodes 4162 and 4164 connected in cascade, i.e., with the anode of the diode 4164 connected to the cathode of the diode 4162, wherein a capacitance $C_P$ is associated with the intermediate point between the two diodes 4162 and 4164.

In the embodiment considered, the rectification circuit 416c comprises moreover switching means configured to connect either:
the anode of the diode 4162 to the node G and the cathode of the diode 4164 to the node S, thereby permitting a discharging of the gate-source capacitance $C_{GS}$, or
the anode of the diode 4162 to the node S and the cathode of the diode 4164 to the node G, thereby permitting a charging of the gate-source capacitance $C_{GS}$.

For example, in the embodiment considered, two p-channel transistors 4168 and 4172 are connected in series between the nodes G and S, wherein the body diode of the two transistors are opposite and directed to the intermediate point between the transistors 4168 and 4172. Similarly, in the embodiment considered, two n-channel transistors 4170 and 4174 are connected in series between the nodes G and S, wherein the body diode of the two transistors are opposite and directed to the intermediate point between the transistors 4170 and 4174.

In the embodiment considered, the anode of the diode 4162 is connected (e.g., directly) to the intermediate point between the transistors 4170 and 4174 and the cathode of the diode 4164 is connected (e.g., directly) to the intermediate point between the transistors 4168 and 4172.

In the embodiments considered, the gates of the transistors 4168 and 4170 are connected to the node G, and the gates of the transistors 4172 and 4174 are connected to the node S. Accordingly, when the gate-source voltage $V_{GS}$ is greater than the threshold voltage $V_{TH}$ of the transistors (see FIG. 19a), the transistors 4168 and 4174 are opened and the transistors 4170 and 4172 are closed, i.e., the diodes 4162 and 4164 are connected between the node S and the node G, thereby permitting only a charging of the node G. Conversely, when the source-gate voltage $V_{SG}=-V_{GS}$ is greater than the threshold voltage $V_{TH}$ (i.e., $V_{GS}<-V_{TH}$) of the transistors (see FIG. 19b), the transistors 4168 and 4174 are closed and the transistors 4170 and 4172 are opened, i.e., the diodes 4162 and 4164 are connected between the node G and the node S, thereby permitting only a discharging of the node G. Generally, the transistors 4168, 4170, 4172 and 4174 could also be driven as a function of the signals SET and RESET in order to achieve a substantially similar operation.

Accordingly, in the embodiments considered, the rectification circuits 416a, 416b and 416c are configured to:
when the switch 400 is on, i.e., when the gate-source voltage $V_{GS}$ is high:
a) when a positive transition is applied to the node T1, transfer charge from the node S to a capacitance $C_P/C_{P1}$, while inhibiting a transfer of charge from the node G to the capacitance $C_P/C_{P1}$, and
b) when a negative transition is applied to the node T1, transfer charge from the capacitance $C_P/C_{P1}$ to the node G; and
when the switch 400 is off, i.e., when the gate-source voltage $V_{GS}$ is low:
a) when a negative transition is applied to the node T1, transfer charge from the capacitance $C_P/C_{P2}$ to the node S, while inhibiting a transfer of charge from the node G to the capacitance $C_P/C_{P2}$, and b) when a positive transition is applied to the node T1, transfer charge from the node G to the capacitance $C_P/C_{P2}$.

Specifically, in the rectifications circuits 416a, 416b and 416c, this is achieved by means of switching means configured:

a) when the switch 400 is on, i.e., when the gate-source voltage $V_{GS}$ is high, connect two diodes 4162 and 4164 between the node G and the node S, wherein the diodes 4162 and 4164 are connected in cascade (i.e., the anode of the second diode 4164 is connected to the cathode of the first diode 4162), and wherein a capacitance $C_P/C_{P1}$ is associated with the intermediate point between the diodes 4162/4164, such that a conductive path is created permitting a current flow only from the node S to the node G, and b) when the switch 400 is off, i.e., when the gate-source voltage $V_{GS}$ is low, connect two diodes 4162 and 4164 between the node S and the node G, wherein the diodes 4162 and 4164 are connected in cascade (i.e., the anode of the second diode 4164 is connected to the cathode of the first diode 4162), and wherein a capacitance $C_P/C_{P2}$ is associated with the intermediate point between the diodes 4162/4164, such that a conductive path is created permitting a current flow only from the node G to the node S.

In the embodiments considered, the rectifications circuits 414a and 414b use two separate branches and switching means (4166 or 4168/4170) configured to enable one of these branches. Conversely, the rectifications circuit 414c comprises a single branch and switching means (4168-4174) configured to change the orientation of this branch between the nodes G and S.

Figure 20:
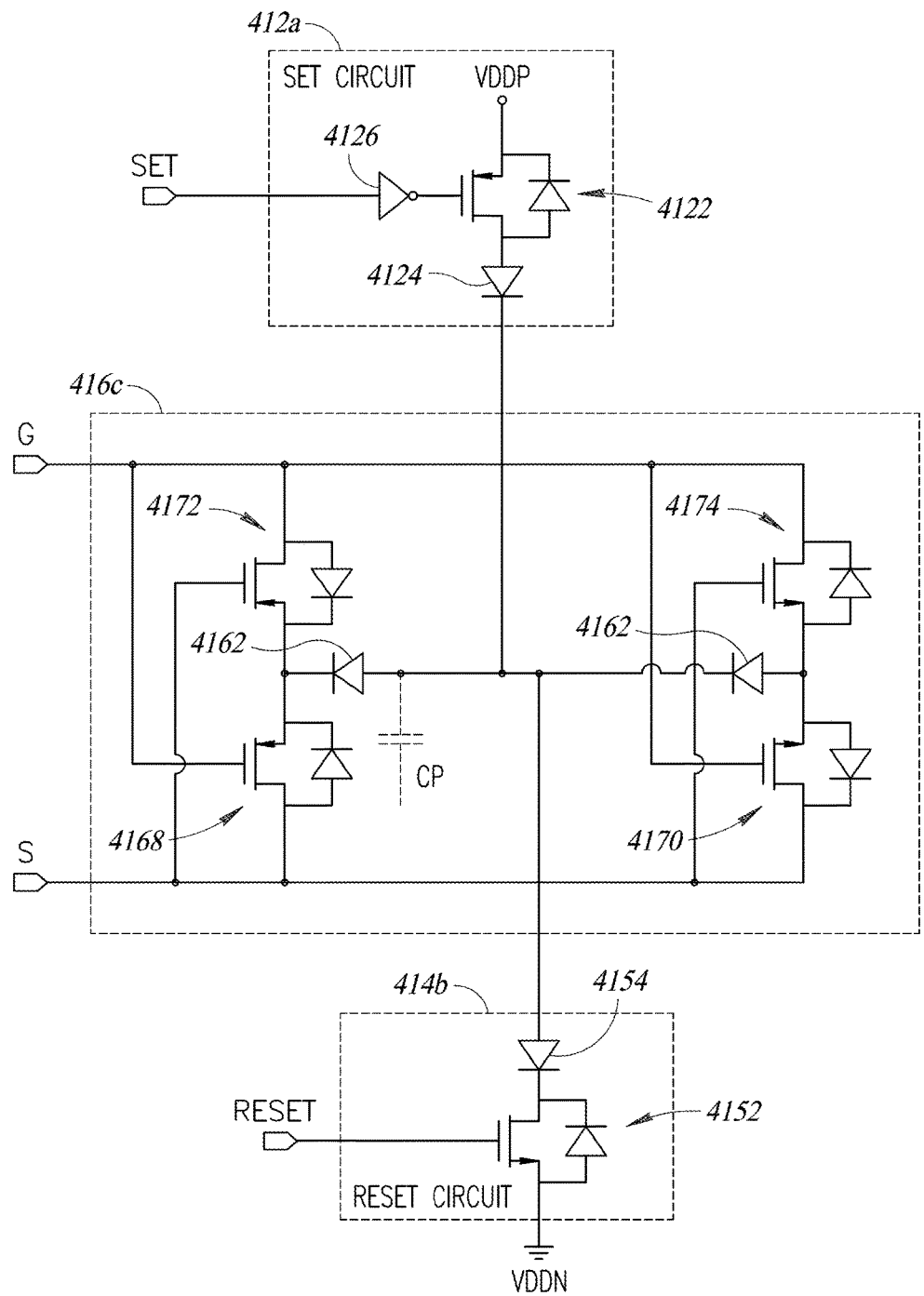
FIGS. 20, 21a and 21b show a fourth embodiment of a rectification circuit adapted to maintain the state of a high voltage switching circuit.

FIG. 20 shows a further embodiment, highlighting that the set circuit 412a and the reset circuit 414b are not necessarily connected directly to the node G as shown in FIGS. 11 and 12. The connection of the circuits 412b and 414a will not be repeated at this point and reference can be made to FIGS. 8 to 12 for this purpose.

Specifically, in the embodiment considered, the circuits 412a and 414b are connected to the intermediate point between the diodes 4162 and 4164.

Figure 21A:
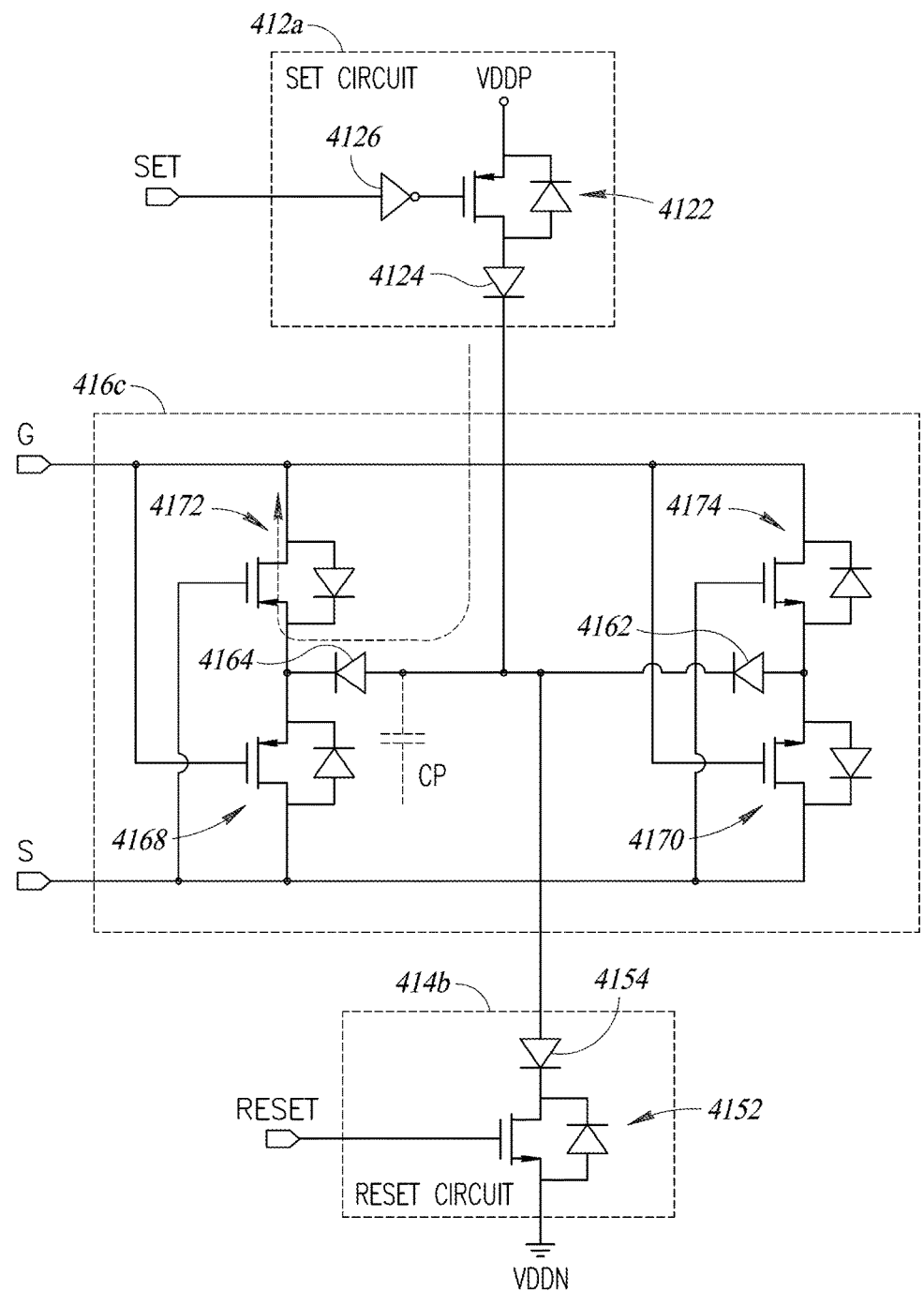

Accordingly, as shown in FIG. 21a, when the switch has to be closed (with the signal SET being set, e.g., to high), the circuit 412a will apply a positive voltage to the anode of the diode 4164. In case the gate-source voltage $V_{GS}$ is low, this positive voltage will switch on the transistor 4172 and the node G will be charged. For this reason, the diode 4164 may also be an active diode driven by means of the signal SET.

Figure 21B:
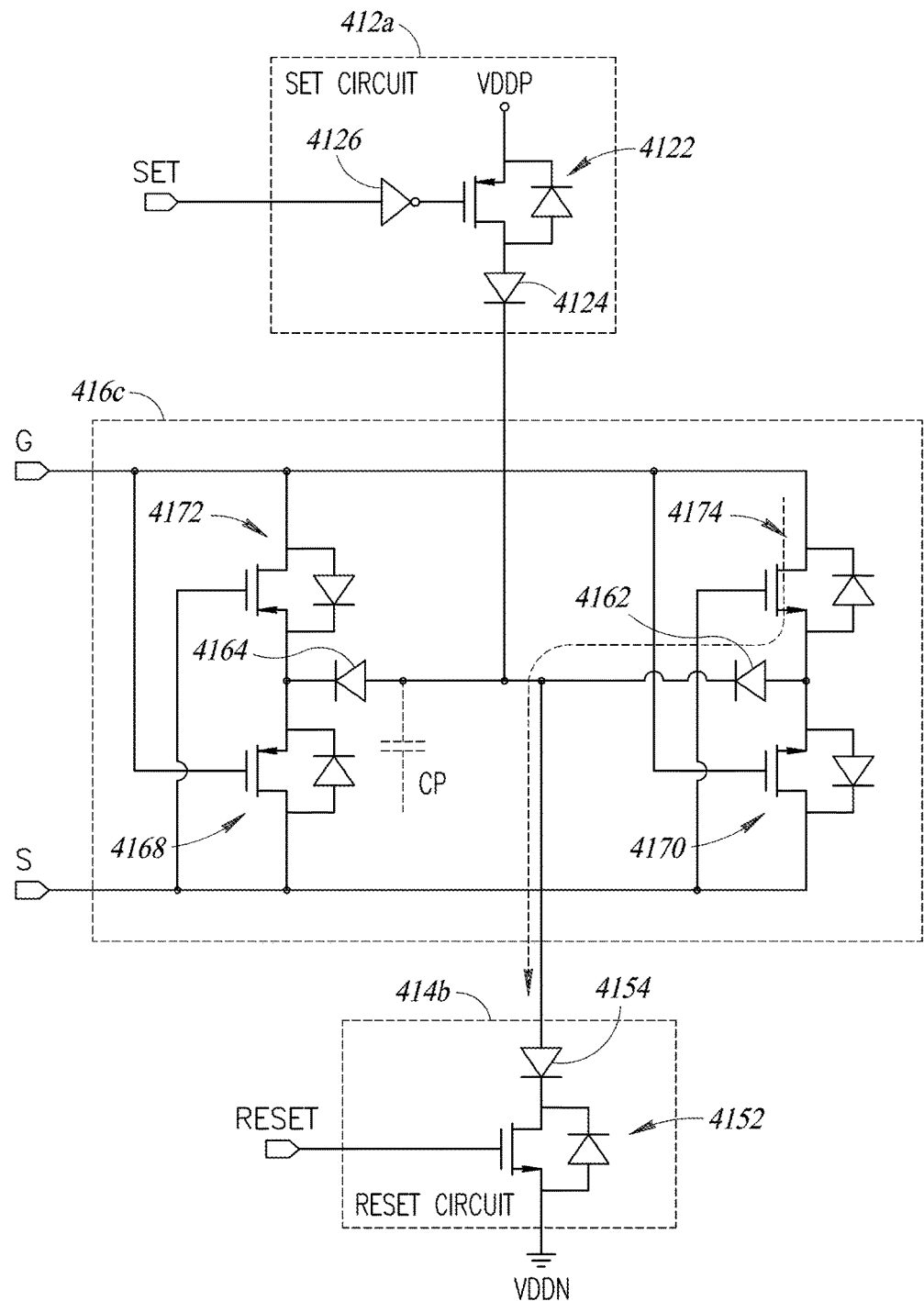

Conversely, as shown in FIG. 21b, when the switch has to be closed (with the signal RESET being set, e.g., to high), the circuit 414b will apply preferably a negative voltage to the cathode of the diode 4162. In case the gate-source voltage $V_{GS}$ is high, this negative voltage will switch on the transistor 4174 and the node G will be discharged. For this reason, the diode 4162 may also be an active diode driven by means of the signal RESET.

The same solution may also be used in the circuit 416a shown in FIG. 13. For example, the circuit 412a may be connected to the anode of the diode $4164_1$ (being possibly an active diode driven by means of the signal SET) and the circuit 414b may be connected to the cathode of the diode $4162_2$ (being possibly an active diode driven by means of the signal RESET).

The above embodiments have the advantage that the active diodes 4124, $4164/4164_1$, 4154 and $4162/4162_2$ are preferably high-voltage active diodes implemented, e.g., with power MOSFET having a complex structure and high parasitic capacitances, thereby generating automatically a high parasitic capacitance $C_P/C_{P1}/C_{P2}$ at the intermediate point between the diodes.

Of course, without prejudice to the principles of the present disclosure, the details of construction and the embodiments may vary widely with respect to what has been described and illustrated herein purely by way of example, without thereby departing from the scope of the present disclosure. For example, while the solutions in the forgoing have been described with regards to n-channel transistors SW1 and SW2, also p-channel transistors could be used, e.g., by exchanging the signals SET and RESET.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. Switching circuitry, comprising:
a first and a second transistor connected in series between two terminals, wherein said first and said second transistor include a respective control terminal connected to a common control node, wherein a capacitance is connected between said common control node and an intermediate point between said first and said second transistor, and wherein said first and said second transistor are rendered conductive or non-conductive as a function of a voltage across said capacitance; and
a control circuit comprising:
a first circuit configured to charge said capacitance as a function of a first control signal, and
a second circuit configured to discharge said capacitance as a function of a second control signal;
a third circuit comprising a plurality of diodes and at least one switch configured, responsive to the voltage across said capacitance being greater than a given threshold value, to connect two diodes in cascade between said intermediate point and said common control node and enable current flow from said intermediate point to said common control node, and responsive to the voltage across said capacitance being smaller than said given threshold value, to connect two diodes in series between said common control node and said intermediate point and enable current flow from said common control node to said intermediate point.

2. The switching circuitry according to claim 1, wherein said first and said second transistor are n-channel Field Effect Transistors, wherein said first control signal indicates that said first and said second transistor should be conductive and said second control signal indicates that said first and said second transistor should be non-conductive.

3. The switching circuitry according to claim 2, wherein said third circuit comprises:
a first branch comprising a first and a second diode connected in cascade,
a second branch comprising a third and a fourth diode connected in cascade, and
at least one switch configured to selectively connect either said first branch or said second branch between said common control node and said intermediate point.

4. The switching circuitry according to claim 3, wherein said at least one switch is driven as a function of the voltage at said capacitance.

5. The switching circuitry according to claim 4, wherein said at least one switch comprises:
- an n-channel Field Effect Transistor connected in series with said first branch between said intermediate point and said common control node, wherein the gate of said n-channel Field Effect Transistor is connected to said common control node, and
- a p-channel Field Effect Transistor connected in series with said second branch between said common control node and said intermediate point, wherein the gate of said p-channel Field Effect Transistor is connected to said common control node.

6. The switching circuitry according to claim 1, wherein said third circuit comprises:
- a first and a second n-channel Field Effect Transistor connected in series between said common control node and said intermediate point, and
- a first and a second p-channel Field Effect Transistor connected in series between said common control node and said intermediate point, and
- a first and a second diode connected in cascade, wherein the anode of said first diode is connected to the intermediate point between said first and said second n-channel Field Effect Transistor and the cathode of said second diode is connected to the intermediate point between said first and said second p-channel Field Effect Transistor.

7. The switching circuitry according to claim 6, wherein:
the gate of said first n-channel Field Effect Transistor is connected to said common control node,
the gate of said second n-channel Field Effect Transistor is connected to said intermediate point,
the gate of said first p-channel Field Effect Transistor is connected to said common control node, and
the gate of said second n-channel Field Effect Transistor is connected to said intermediate point.

8. The switching circuitry according to claim 7, wherein said first circuit comprises:
- a first sub-circuit configured to selectively apply a first voltage to said common control node, and
- a second sub-circuit configured to selectively apply a second voltage to said intermediate point, said first voltage being greater than said second voltage.

9. The switching circuitry according to claim 8, wherein said second circuit comprises:
- a first sub-circuit configured to selectively apply a first voltage to said intermediate point, and
- a second sub-circuit configured to selectively apply a second voltage to said common control node, said first voltage being equal to or greater than said second voltage.

10. The switching circuitry according to claim 9, wherein said first sub-circuit of said first circuit and/or said second sub-circuit of said second circuit are connected to the intermediate point between first and said second diode.

11. A method of switching a high voltage signal, comprising:
applying an oscillating high-voltage drive signal to an input node;
coupling the high-voltage drive signal to an output node through two series-connected transistors, the series-connected transistors having a common control node and signal nodes coupled between the input and output nodes with an intermediate node being defined at the interconnection of the signal nodes of the series-connected transistors;
coupling a plurality of series-connected diodes between the common control node and the intermediate node to provide current flow from the intermediate node to the common control node responsive to a transition of the high-voltage drive signal on the input node from a first level to a second level if a voltage across the common control node and the intermediate node exceeds a threshold voltage of the series-connected transistors; and
coupling a plurality of series-connected diodes between the common control node and the intermediate node to provide current flow from the common control node to the intermediate node responsive to a transition of the high-voltage drive signal from the second level to the first level if the voltage across the common control node and the intermediate node is less than the threshold voltage of the series-connected transistors.

12. The method of claim 11, wherein coupling a plurality of series-connected diodes between the common control node and the intermediate node comprises:
coupling first and second diodes between the common control node and the intermediate node; and
charging a parasitic capacitance of a parasitic intermediate node defined between the first and second diodes.

13. The method of claim 12, wherein charging a parasitic capacitance of a parasitic intermediate node defined between the first and second diodes comprises charging the parasitic capacitance to prevent the flow of current from the common control node to the intermediate node responsive to transitions of the high-voltage drive signal when the threshold voltage across the common control node and the intermediate node exceeds the threshold voltage of the series-connected transistors.

14. The method of claim 13, wherein charging a parasitic capacitance of a parasitic intermediate node defined between the first and second diodes comprises charging the parasitic capacitance to prevent the flow of current from the intermediate node to the common control node responsive to transitions of the high-voltage drive signal when the threshold voltage across the common control node and the intermediate node is less than threshold voltage of the series-connected transistors.

15. An electronic system, comprising:
at least one transducer;
signal generation circuitry;
analysis circuitry; and
an integrated circuit including switching circuitry coupled between the at least one transducer and the analysis and signal generation circuitry, the switching circuitry including:
- a first transistor and a second transistor coupled in series between an input node and an output node, each of the first and second transistors having a control node coupled to a common control node and having a first signal node coupled to an intermediate node, a second signal node of the first transistor being coupled to the input node and a second signal node of the second transistor coupled to the output node; and
- a control circuit coupled to the common control node and to the intermediate node and configured to receive a control signal indicating whether the first and second transistors are conductive to close the switching circuitry or are non-conductive to open the switching circuitry, the control circuit including a plurality of diodes configured to be coupled between the common control node and the intermediate node to provide current flow from the intermediate node to the common control node responsive to a transition of a drive signal on the input node from a first level to a second level if a voltage across the common control node and the intermediate node exceeds a threshold voltage of the first and second transistors, and the control circuit including a plurality of diodes configured to be coupled between the common control node and the intermediate node to provide current flow from the common control node to the intermediate node responsive to a transition of the drive signal from the second level to the first level if the voltage across the common control node and the intermediate node is less than the threshold voltage of the first and second transistors.

16. The electronic system of claim 15, wherein the electronic system comprises an echography system and the signal generation circuitry comprises a pulser circuit, and wherein the at least one transducer comprises an array of capacitive micromachined ultrasound transducers or piezoelectric transducers.

17. The electronic system of claim 16, wherein each of the first and second transistor comprises an n-channel field effect transistor having a source node coupled to the intermediate node and having a gate node coupled to the common control node, and a drain of the first transistor coupled to the input node and a drain of the second transistor coupled to the output node.

18. The electronic system of claim 17, wherein the plurality of diodes includes first and second series coupled diodes having a first parasitic intermediate node defined between the first and second series coupled diodes, the first parasitic intermediate node having a parasitic capacitance that is charged to prevent the flow of current from the common control node to the intermediate node responsive to transitions of the drive signal if the threshold voltage across the common control node and the intermediate node exceeds the threshold voltage of the first and second transistors.

19. The electronic system of claim 18, wherein the plurality of diodes includes third and fourth series coupled diodes having a second parasitic intermediate node defined between the third and fourth series coupled diodes, the second parasitic intermediate node having a parasitic capacitance that is charged to prevent the flow of current from the intermediate node to the common control node responsive to transitions of the drive signal if the threshold voltage across the common control node and the intermediate node is less than the threshold voltage of the first and second transistors.

20. The electronic system of claim 10, wherein each of the plurality of diodes comprises an active diode.

21. The switching circuitry of claim 1, wherein each of the first and second transistors comprises a field effect transistor having a gate node and a source node, and wherein the capacitance corresponds to gate-to-source capacitances of the field effect transistors.

22. The switching circuity of claim 21, wherein the control circuit further comprises a switch configured to control coupling of the pluralities of diodes between the common control and intermediate nodes based upon a gate-to-source voltage of the field effect transistors.

* * * * *